US011707592B2

(12) United States Patent
Assani

(10) Patent No.: US 11,707,592 B2
(45) Date of Patent: Jul. 25, 2023

(54) DEVICE AND METHOD OF GENERATING AN ENRICHED GAS WITHIN A NASAL VESTIBULE

(71) Applicant: Worldwide Health Innovations, LLC, Cincinnati, OH (US)

(72) Inventor: Keavash Darren Assani, Cincinnati, OH (US)

(73) Assignee: Worldwide Health Innovations, LLC, Cincinnati, OH (US)

( * ) Notice: Subject to any disclaimer, the term of this patent is extended or adjusted under 35 U.S.C. 154(b) by 941 days.

(21) Appl. No.: 16/587,962

(22) Filed: Sep. 30, 2019

(65) Prior Publication Data

US 2021/0093821 A1    Apr. 1, 2021

(51) Int. Cl.
*A61M 16/06* (2006.01)
*A61M 16/10* (2006.01)
*A61M 16/20* (2006.01)
*A61M 16/00* (2006.01)

(52) U.S. Cl.
CPC .... *A61M 16/0672* (2014.02); *A61M 16/0072* (2013.01); *A61M 16/101* (2014.02); *A61M 16/208* (2013.01); *A61M 2205/3584* (2013.01); *A61M 2205/7545* (2013.01); *A61M 2205/8206* (2013.01); *A61M 2210/0618* (2013.01); *A61M 2230/04* (2013.01); *A61M 2230/20* (2013.01);
(Continued)

(58) Field of Classification Search
CPC .......... A61M 16/0072; A61M 16/0672; A61M 16/101; A61M 16/105; A61M 16/106; A61M 16/107; A61M 2210/0618; A62B 23/06; A62B 19/00; A62B 19/02
See application file for complete search history.

(56) References Cited

U.S. PATENT DOCUMENTS

| 4,221,217 A * | 9/1980 | Amezcua ............... A62B 23/06 128/203.22 |
| 6,802,489 B2 | 10/2004 | Marr et al. |
| 8,366,815 B2 | 2/2013 | Taylor et al. |

(Continued)

OTHER PUBLICATIONS

Chai, S.W., et al., "Rapid Pressure Swing Adsorption for Reduction of Bed Size Factor of a Medical Oxygen Concentrator," Ind. Eng. Chem. Res., 2011, 50:8703-8710, 8 pgs.
(Continued)

*Primary Examiner* — Valerie L Woodward
(74) *Attorney, Agent, or Firm* — Frost Brown Todd LLP

(57) ABSTRACT

A device and method of generating an enriched gas within a nasal vestibule of a patient includes a housing, a chamber, a chamber inlet, a pump, a molecular sieve bed, a release outlet, and a breath duct. The chamber is configured to be received within the nasal vestibule. The pump is configured to direct an ambient air from an ambient environment into the chamber. The molecular sieve bed is positioned within the chamber and configured to collect a predetermined molecule from the ambient air thereby generating the enriched gas. The release outlet is configured to discharge the enriched gas from the chamber into the nasal vestibule. The breath duct longitudinally extends through the housing such that the breath duct is configured to fluidly communicate a fluid flow through the housing for nasal breathing by the patient while the chamber is positioned within the nasal vestibule.

19 Claims, 13 Drawing Sheets

(52) U.S. Cl.
CPC ..... *A61M 2230/42* (2013.01); *A61M 2230/62* (2013.01)

(56) References Cited

U.S. PATENT DOCUMENTS

| | | | | |
|---|---|---|---|---|
| 10,987,527 | B1* | 4/2021 | Gray | A62B 18/006 |
| 2003/0106555 | A1* | 6/2003 | Tovey | A61F 5/08 |
| | | | | 128/205.27 |
| 2003/0106556 | A1* | 6/2003 | Alperovich | A62B 23/06 |
| | | | | 128/205.27 |
| 2015/0000670 | A1* | 1/2015 | Kim | A62B 9/06 |
| | | | | 128/206.11 |
| 2019/0232217 | A1* | 8/2019 | Kirkbride | B01D 63/12 |
| 2020/0206547 | A1* | 7/2020 | Hellman | A62B 23/06 |

OTHER PUBLICATIONS

Choong, T.S.Y., et al., "The linear driving force model for cyclic adsorption and desorption: the effect of external fluid-film mass transfer," Chemical Engineering Science, 1998, 53(4):847-851, 5 pgs.

Debray, A., et al., "A passive micro gas regulator for hydrogen flow control," J. Micromech. Microeng., 2005, 15:S202-S209, 8 pgs.

Farooq, S., et al., "A Predictive Model for A Kinetically Controlled Pressure Swing Adsorption Separation Process," Chemical Engineering Science, 1993, 48(24):4129-4141, 13 pgs.

Grande, C.A., "Advances in Pressure Swing Adsorption for Gas Separation," ISRN Chemical Engineering, 2012, vol. 2012, Article ID 982934, 13 pgs.

Interra Global Corporation. mSORB® Safety Data Sheet, Mar. 2015, 3 pgs.

Kopaygorodsky, E.M., et al., "Predictive Dynamic Model of Single-Stage Ultra-Rapid Pressure Swing Adsorption," AIChE Journal, May 2004, 50(5):953-962, 10 pgs.

Ojuva, A., "Processing and performance of zeolites for efficient carbon dioxide separation," Department of Materials and Environmental Chemistry, Stockholm University, Stockholm, Sweden, Doctoral Thesis, 2015, 83 pgs.

Pan, M., et al., "Application of Nanosize Zeolite Molecular Sieves for Medical Oxygen Concentration," Nanomaterials, 2017, 7:195, 19 pgs.

Parmar, A., et al., "Wireless Charging," The Startup, Medium, Feb. 2018, 17 pgs., downloaded from <https://medium.com/swlh/wireless-charging-c0a35351ffe8?>.

Pikul, J.H., et al., "High-power lithium ion microbatteries from interdigitated three-dimensional bicontinuous nanoporous electrodes," Nature Communications, Apr. 2013, 4:1732, 5 pgs.

Rezaei, F., et al., "Structured adsorbents in gas separation process," Separation and Purification Technology, 2010, 70:243-256, 14 pgs.

Sahlstrand-Johnson, P., et al., "Computed tomography measurements of different dimensions of maxillary and frontal sinuses," BMC Medical Imaging, 2011, 11:8, 7 pgs.

Suzuki, M., et al., "Piston-Driven Ultra Rapid Pressure Swing Adsorption," Adsorption, 1996, 2:111-119, 9 pgs.

Teague, Jr., K.G., et al., "Predictive Dynamic Model of a Small Pressure Swing Adsorption Air Separation Unit," Ind. Eng. Chem. Res., 1999, 38:3761-3775, 15 pgs.

\* cited by examiner

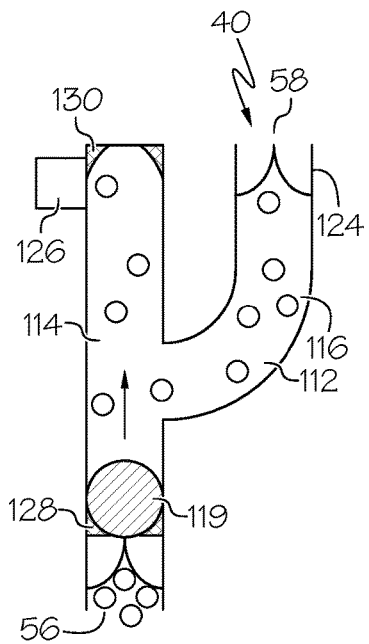 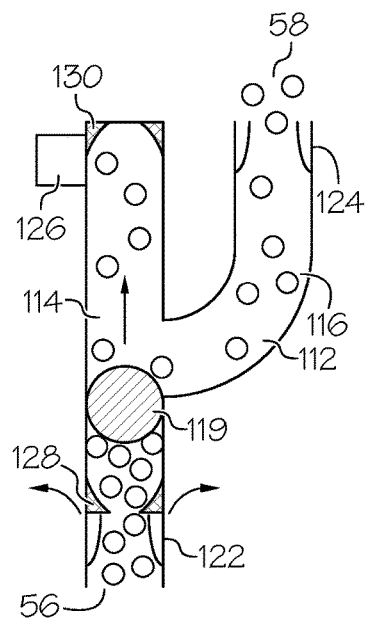 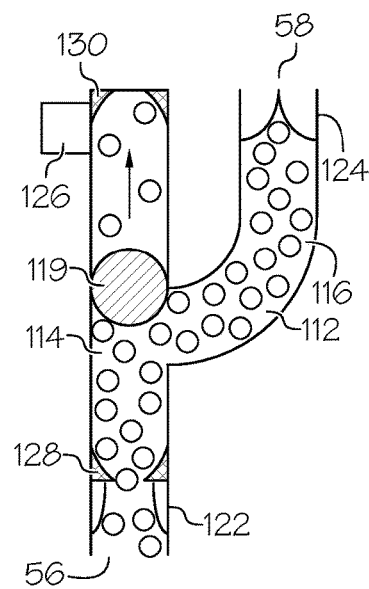
FIG. 6A    FIG. 6B    FIG. 6C
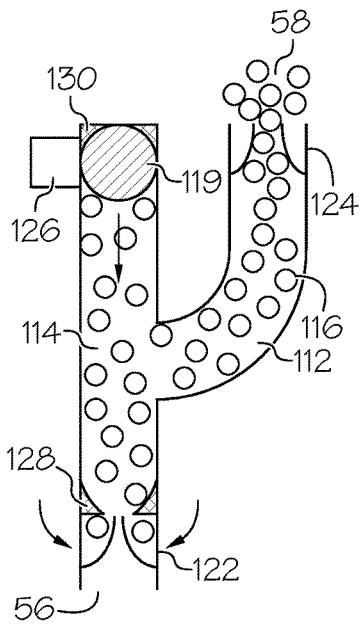 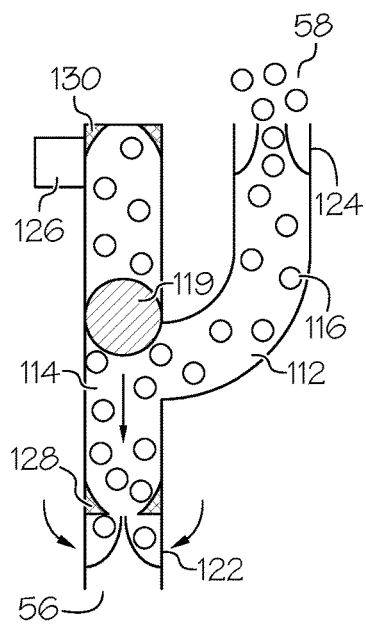
FIG. 6D    FIG. 6E

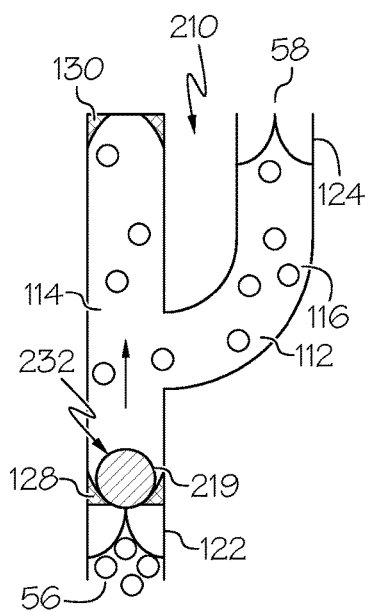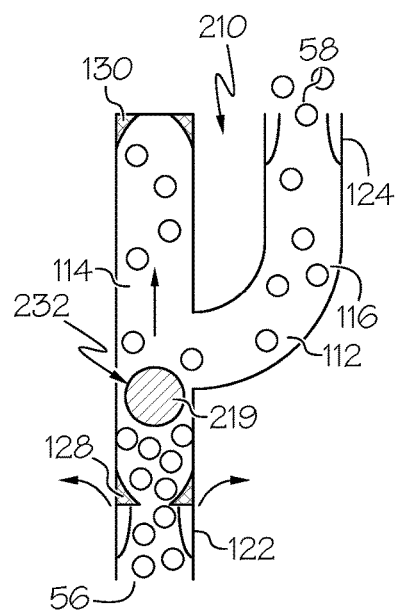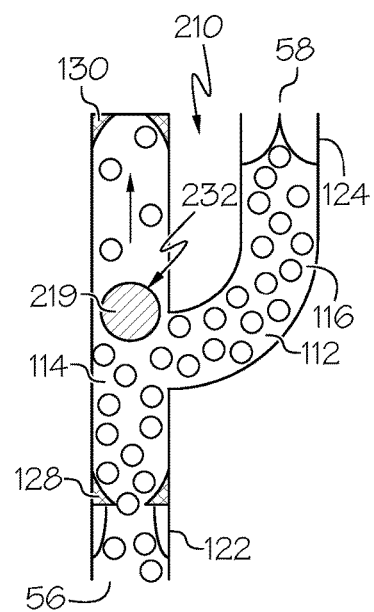
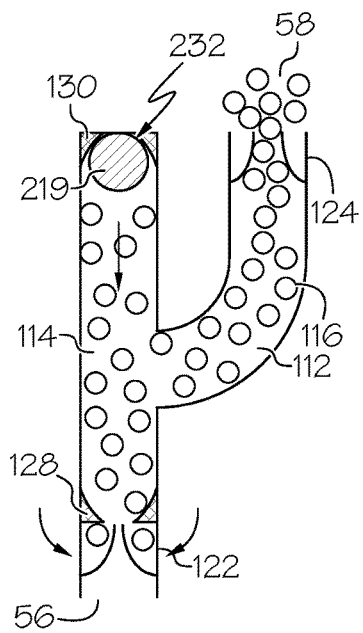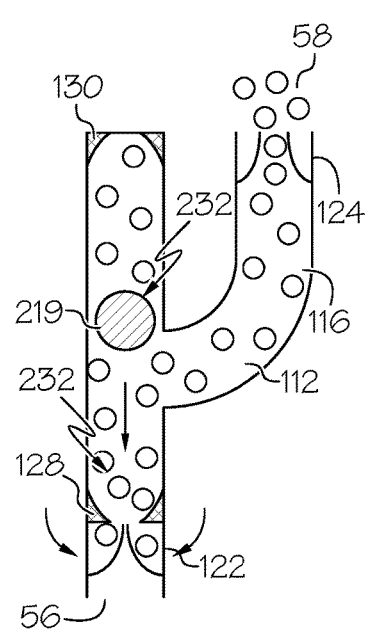
FIG. 7A  FIG. 7B  FIG. 7C
FIG. 7D  FIG. 7E

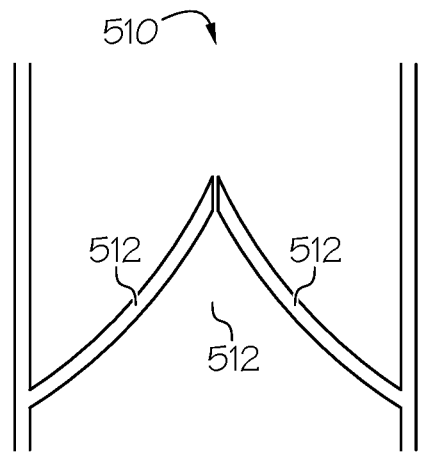
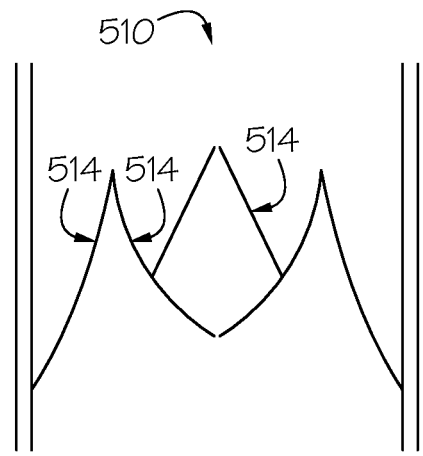
FIG. 11A  FIG. 11B
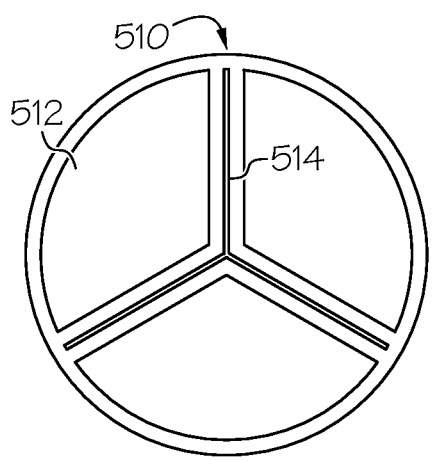
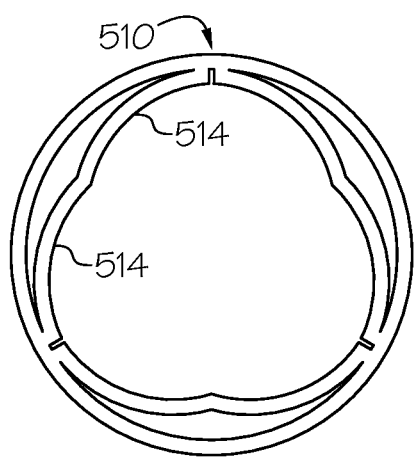
FIG. 12A  FIG. 12B

DEVICE AND METHOD OF GENERATING AN ENRICHED GAS WITHIN A NASAL VESTIBULE

TECHNICAL FIELD

The present invention relates generally to a device and method of generating an enriched gas from an ambient gas and, more particularly, to a device and method of generating an oxygen enriched gas for use by a patient.

BACKGROUND

Portable oxygen tanks and portable oxygen concentrators supply an oxygen enriched gas to patients having relatively low blood oxygen levels. In turn, the blood oxygen levels of the patient increase while breathing with the aid of the oxygen enriched gas in order to provide improved patient outcomes, such as greater comfort, improved physical and mental activity, and even increased lifespan.

Portable oxygen tanks contain high pressure oxygen for the patient to breath the oxygen enriched gas. In order to contain this oxygen at sufficient volumes for use, these portable oxygen tanks tend to be relatively heavy and may be attached to a cart to aid patient mobility. A pressure regulator fitted to the oxygen tank reduces the pressure to a breathable pressure, but such regulators are expensive and contribute to the overall weight of the oxygen tank. Additional valves control the flow of the oxygen through hoses fitted between the oxygen tank and the patient's nose. Once the oxygen is consumed from the oxygen tank during use, the oxygen tank must be refilled with oxygen for reuse, which occurs relatively frequently, particularly when the patient uses a smaller tank with reduced weight for increased mobility. In any case, patients often must limit travel to return home or pack replacement oxygen tanks, which may be difficult for an injured or infirm patient to wield.

Portable oxygen concentrators draw upon ambient air in order to generate the oxygen enriched gas outside of the patient so as to avoid the use of portable oxygen tanks. While reducing the likelihood of constantly replacing portable oxygen tanks may improve patient mobility in some cases, the overall weight of the portable oxygen concentrators remains relatively heavy and comparable to portable oxygen tanks. Moreover, like portable oxygen tanks, portable oxygen concentrators also have cumbersome hoses fitted between the portable oxygen concentrators and the patient's nose. The hoses are supported by resting a distal end of the hoses on the upper lip and suspending the hoses over the top of both ears and under the chin in a noose like manner. These hoses and overall weight of the portable oxygen concentrator remain uncomfortable, hindering the mobility of the patient. Additionally, these hoses can lead to pressure sores and infections, are not aesthetically pleasing, and can lead to embarrassment and insecurity of the patient in public.

There is a need for a device and method of providing an enriched gas, particularly an oxygen enriched gas to a patient, that is lighter, less cumbersome than portable oxygen concentrators, particularly an oxygen generator that addresses present challenges and characteristics such as those discussed above.

SUMMARY

A device for generating an enriched gas, such as an oxygen enriched gas, within a nasal vestibule of a patient includes a housing, a first chamber, at least a first chamber inlet, at least a first pump, a first molecular sieve bed, a first release outlet, and a first breath duct. The housing has a distal housing portion and a proximal housing portion. The first chamber is positioned within the housing and configured to be received within the nasal vestibule of the patient. The at least the first chamber inlet is fluidly connected to the first chamber. The at least the first pump is fluidly connected to the at least the first chamber inlet and configured to direct an ambient air from an ambient environment into the first chamber via the at least the first chamber inlet. The first molecular sieve bed is positioned within the first chamber and configured to collect a predetermined molecule from the ambient air thereby generating the enriched gas. The first release outlet is fluidly connected to the first chamber and configured to discharge the enriched gas from the first chamber into the nasal vestibule. The first breath duct longitudinally extends through the housing and has a first distal duct opening and a first proximal duct opening. The first distal duct opening is positioned in the distal housing portion, whereas the first proximal duct opening is positioned in the proximal housing portion. Thereby, the first breath duct is configured to fluidly communicate a first fluid flow through the housing for nasal breathing through the housing by the patient while the first chamber is positioned within the nasal vestibule of the patient.

Furthermore, a device for generating an enriched gas, such as an oxygen enriched gas, within a nasal vestibule of a patient includes a housing, a first chamber, at least a first chamber inlet, a plurality of first pumps, a first molecular sieve bed, and a first release outlet. The housing has a distal housing portion and a proximal housing portion. The first chamber is positioned within the housing and configured to be received within the nasal vestibule of the patient. The at least the first chamber inlet is fluidly connected to the first chamber. The plurality of first pumps is connected to the at least the first chamber inlet and configured to direct an ambient air from an ambient environment into the first chamber via the at least the first chamber inlet. The first molecular sieve bed is positioned within the first chamber and configured to collect a predetermined molecule from the ambient air thereby generating the enriched gas. The first release outlet is fluidly connected to the first chamber and configured to discharge the enriched gas from the first chamber into the nasal vestibule. Each of the first plurality of first pumps is positioned in the proximal housing portion such that the plurality of first pumps is proximally positioned relative to the first chamber.

In use, a method of generating an enriched gas, such as an oxygen enriched gas, for a patient, includes collecting nitrogen from an ambient air into a molecular sieve bed positioned within a nasal vestibule of the patient thereby generating the oxygen enriched gas within the nasal vestibule of the patient.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 6A depicts a schematic, sectional view of the pressurization pump of FIG. 5 having a piston ball in an initial position of a vacuum stroke in a pressure cycle moving toward a terminal position of the vacuum stroke of the pressure cycle;

FIG. 6B depicts the schematic, sectional view of the pressurization pump similar to FIG. 6A, but with the piston ball in a mid-proximal position of the vacuum stroke before passing a pump duct conduit and drawing an ambient air into the pressurization pump;

FIG. 6C depicts the schematic, sectional view of the pressurization pump similar to FIG. 6B, but with the piston ball in a mid-distal position of the vacuum stroke after passing the pump duct conduit toward the terminal position of the vacuum stroke further drawing the ambient air into the pressurization pump;

FIG. 6D depicts the schematic, sectional view of the pressurization pump similar to FIG. 6C, but with the piston ball in an initial position of a pressure stroke of the pressure cycle moving toward a terminal position of the pressure stroke thereby forcing the ambient air from the pressurization pump;

FIG. 6E depicts the schematic, sectional view of the pressurization pump similar to FIG. 6D, but with the piston ball in the mid-distal position of the pressure stroke before passing by the pump duct conduit toward the terminal position of the pressure stroke further forcing the ambient air from the pressurization pump;

FIG. 7A depicts a schematic, sectional view of a second example of a pressurization pump having a piston ball in an initial position of a vacuum stroke in a pressure cycle moving toward a terminal position of the vacuum stroke of the pressure cycle;

FIG. 7B depicts the schematic, sectional view of the pressurization pump similar to FIG. 7A, but with the piston ball in a mid-proximal position of the vacuum stroke before passing by a pump duct conduit and drawing an ambient air into the pressurization pump;

FIG. 7C depicts the schematic, sectional view of the pressurization pump similar to FIG. 7B, but with the piston ball in a mid-distal position of the vacuum stroke after passing by the pump duct conduit toward the terminal position of the vacuum stroke further drawing the ambient air into the pressurization pump;

FIG. 7D depicts the schematic, sectional view of the pressurization pump similar to FIG. 7C, but with the piston ball in an initial position of a pressure stroke of the pressure cycle moving toward a terminal position of the pressure stroke thereby forcing the ambient air from the pressurization pump;

FIG. 7E depicts the schematic, sectional view of the pressurization pump similar to FIG. 7D, but with the piston ball in the mid-distal position of the pressure stroke passing by the pump duct conduit toward the terminal position of the pressure stroke further forcing the ambient air from the pressurization pump;

FIG. 11A depicts a schematic sectional view of a tricuspid valve in a closed position;

FIG. 11B depicts the schematic sectional view of the tricuspid valve similar to FIG. 11A, but with the tricuspid valve in an open position;

FIG. 12A depicts a schematic end view of the tricuspid valve of FIG. 11A in the closed position;

FIG. 12B depicts the schematic end view of the tricuspid valve similar to FIG. 12A, but with the tricuspid valve in the open position;

Figure 1:
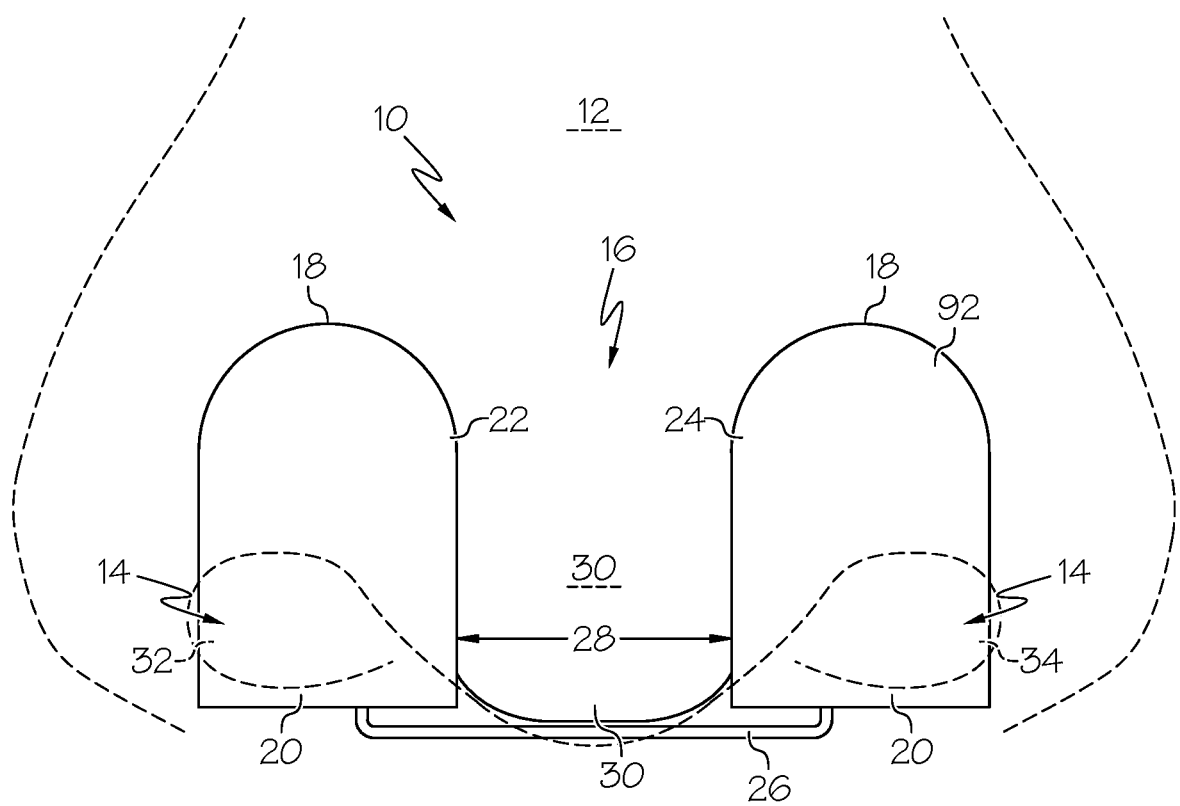
FIG. 1 depicts a front elevational view of an exemplary gas concentration device having a pair of lateral housing bodies respectively received within a left nostril and a right nostril of a nose of a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a patient inserting a gas concentration device into a patient's nasal vestibule. For example, a patient's nostrils are relatively proximal to a remainder of the more distally positioned nasal vestibule within the nose of the patient. It will be further appreciated that, for convenience and clarity, spatial terms such as "left," "right," "side," "axial," and "longitudinal" also are used herein for reference to relative positions and directions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY GAS CONCENTRATION DEVICE FOR A NASAL VESTIBULE

FIG. 1 shows an exemplary gas concentration device (10) received within a nose (12) and configured to generate an enriched gas, such as an oxygen enriched gas, within a nasal vestibule (14) of the patient. The gas concentration device (10) of the present example includes housing (16) having a distal housing portion (18) and an opposing proximal housing portion (20) with a left lateral housing body (22) and a right lateral housing body (24). The left and right lateral housing bodies (22, 24) are laterally spaced apart from each other in a lateral direction, while each of the left and right lateral housing bodies (22, 24) also longitudinally extend in a longitudinal direction from the distal housing portion (18) to the proximal housing portion (20). The proximal housing portion (20) further includes a connection bridge (26) laterally extending between the left lateral housing body (22) and the right lateral housing body (24) and securing the left lateral housing body (22) relative to the right lateral housing body (24). The connection bridge (26), the left lateral housing body (22), and the right lateral housing body (24) collectively define a gap (28) configured to receive a nasal cartilage (30) upon insertion of the left and right lateral housing bodies (22, 24) respectively through a left nostril (32) and a right nostril (34) of the nose (12). While received within the nasal vestibule (14) of the nose (12), the gas concentration device (10) draws upon an ambient air from an ambient environment outside of the nose (12), generates the oxygen enriched gas within the nasal vestibule (14), and discharges the oxygen enrich gas into the nasal vestibule (14) for use by the patient. While the present example of the gas concentration device (10) has a pair of housing bodies (22, 24) received in the nose (12), an alternative example may have one such housing body respectively received within one of the nostrils (32, 34) with or without the accompanying connection bridge (26). It will thus be appreciated that any one or more of housing bodies (22, 24) in any arrangement configured to generate the oxygen enriched gas within the nasal vestibule (14) may be similarly used. Moreover, the housing bodies (22, 24) are shown in the present example as having a majority of the longitudinal length of each respective housing body (22, 24) received within the nose (12), but one or more alternative examples may have less than the majority of the longitudinal length of the housing bodies (22, 24) received within the nose (12) or even have one or more of the housing bodies (22, 24) completely received within the nose (12). The invention is thus not intended to be unnecessarily limited to inserted position of the gas concentration device (10) within the nose (12) as shown and described herein.

Figure 2:
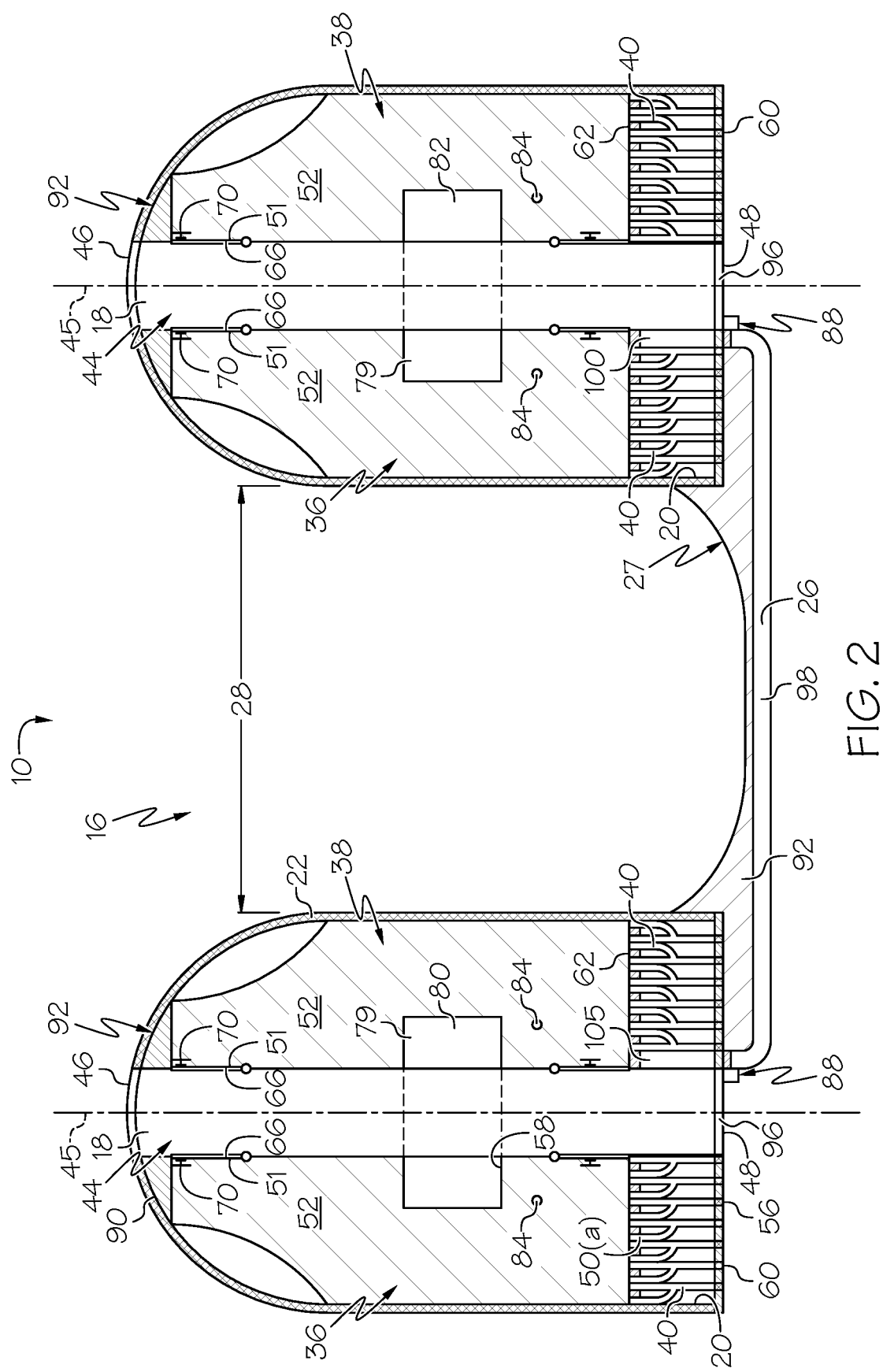
FIG. 2 depicts a cross-sectional view of the gas concentration device of FIG. 1 taken along a pair of axial centerlines of the respective pair of lateral housing bodies.

With respect to FIG. 2, the left and right lateral housing bodies (22, 24) each contain a left chamber (36), and a right chamber (38), a plurality of pressurization and depressurization pumps (40), and a breath duct (44), which longitudinally extends along a longitudinal axis (45) between a distal duct opening (46) in a distal housing portion (18) of lateral housing bodies (22, 24) and a proximal duct opening (48) in the proximal housing portion (20) of lateral housing bodies (22, 24). The pressurization and depressurization pumps (40) respectively connect to a plurality of chamber ports (50a, 50b) (see FIG. 4). Pressurization pumps (40) connect to a plurality of chamber ports (50a), which may also be referred to herein as chamber inlets (50a) as configured to direct the ambient air into the left and right chambers (36, 38). Similarly, the depressurization pumps (40) respectively connect to another plurality of chamber ports (50b) (see FIG. 4), which may also be referred to herein as chamber outlets (50b) (see FIG. 4) as configured to direct a processed gas from the left and right chambers (36, 38) to the ambient environment outside of the nose (12) (see FIG. 1). In addition, each chamber (36, 38) has a release outlet (51) configured to vent the oxygen enriched gas separated from the processed gas into the breath duct (44). The patient inhales the oxygen enriched gas from the breath duct (44). It will thus be appreciated that the terms "inlet" and "outlet" are meant for clarity of use as a "port" and not intended to be respectively limited to use only as an inlet or only as an outlet. In any case, each chamber (36, 38) contains a molecular sieve bed (52) configured to separate the ambient air into the processed gas and the enriched gas. The molecular sieve bed (52) of the present example includes an adsorbent or catalyst, such as zeolite. Zeolite is a microporous, aluminosilicate mineral with a porous structure that can accommodate a wide variety of cations, such as $Na^+$, $K^+$, $Ca^{2+}$, $Mg^{2+}$ and others. Such zeolite is configured to capture portions of the ambient air, such as nitrogen, to form the processed gas and, in turn, generate the enriched gas, such as the oxygen enriched gas.

It will be appreciated to one of ordinary skill that under predetermined conditions, including a predetermined pressure, each molecular sieve bed (52) of zeolite is configured to selectively sort molecules based primarily on affinity. In one example, the affinity of the zeolite has strong ionic forces that allow for the binding of carbon dioxide, monoxide, hydrogen sulfide, nitrogen, and other weak polar molecules. This affinity allows for a high purity oxygen stream. As shown in the present example, the left lateral housing body (36) and its contents have a laterally mirrored arrangement to the right lateral housing body (38) such that it will be appreciated that any discussion of the left lateral housing body (36) and its contents similarly applies to the right lateral housing body (38). Of course, the invention is not intended to be unnecessarily limited to such a mirrored arrangement of like left and right lateral housing bodies (36, 38).

Figure 3:
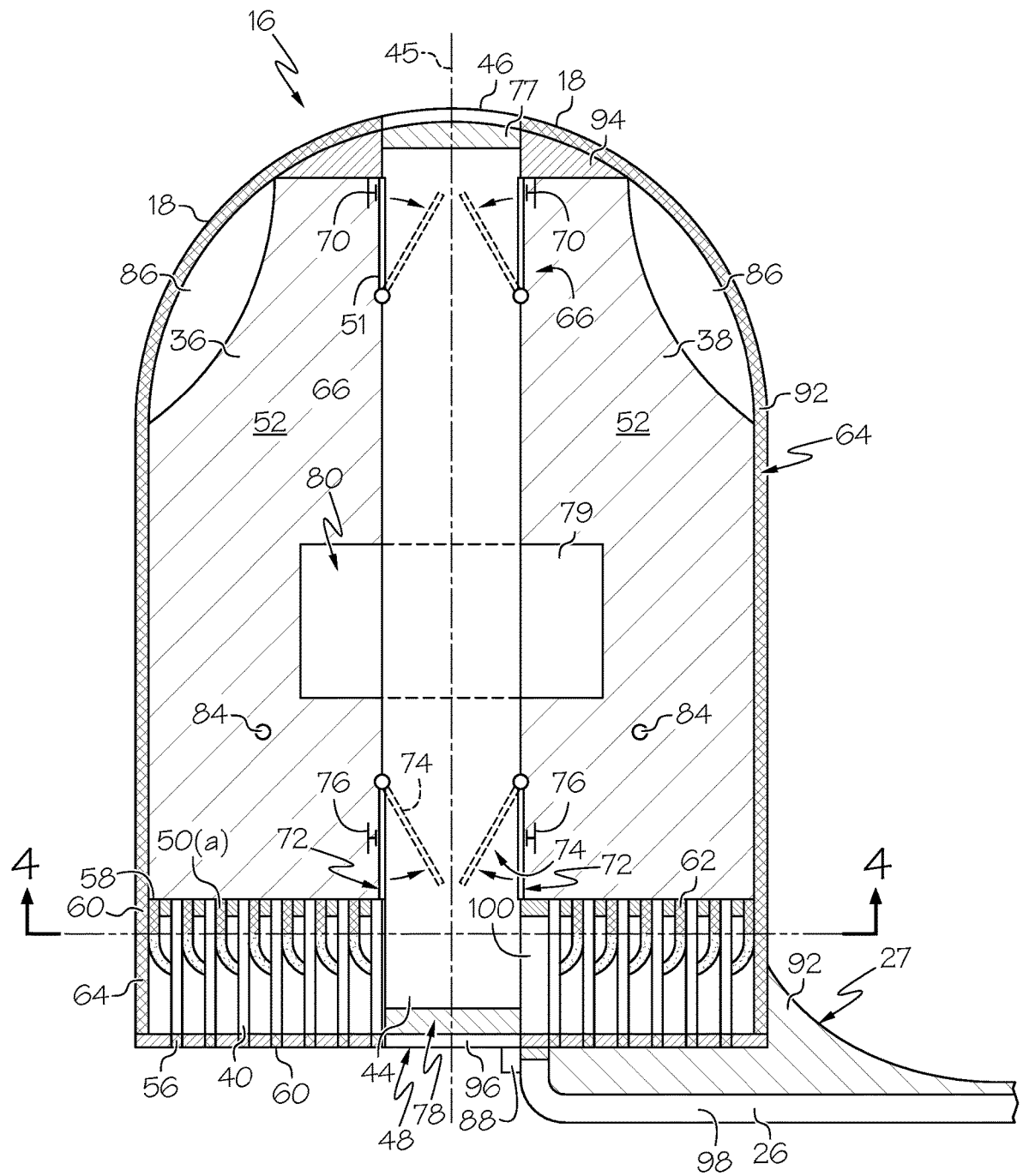
FIG. 3 depicts an enlarged cross-sectional view of the gas concentration device of FIG. 2 with a left lateral housing body configured to be received within the left nostril of the patient.
Figure 4:
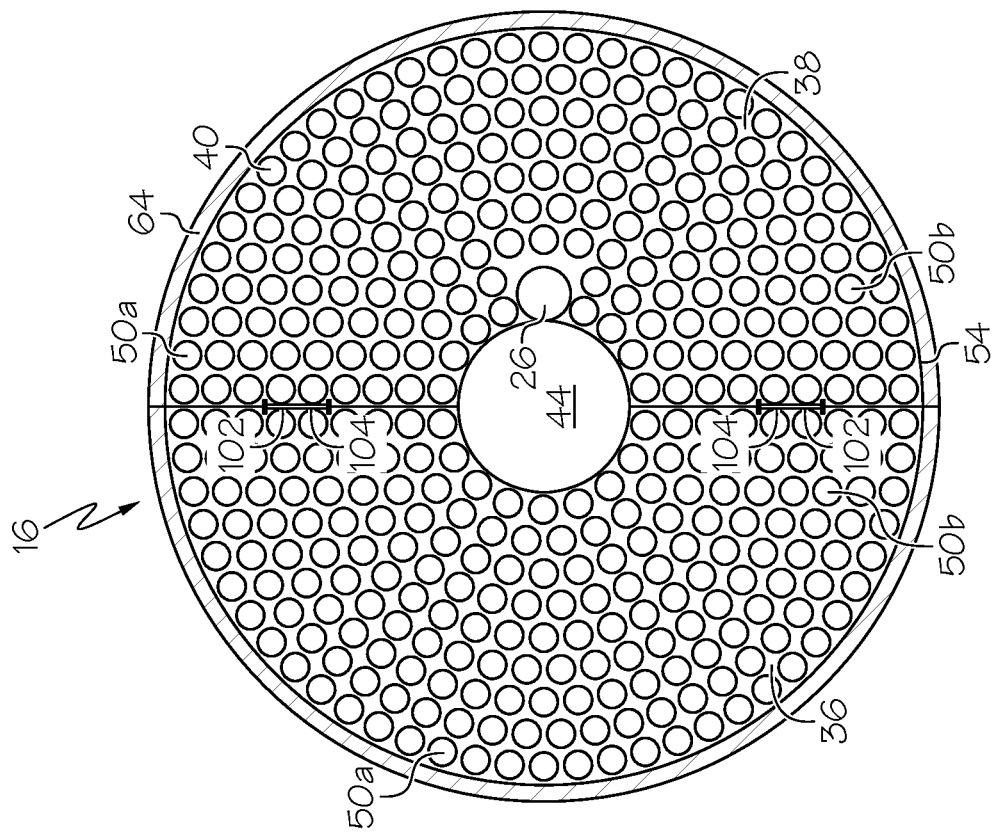
FIG. 4 depicts a cross-sectional view of the gas concentration device of FIG. 1 taken along section line 4-4 of FIG. 3 showing a plurality of pumps.

With respect to FIGS. 2-4 the left chamber (36) is fluidly separated from the right chamber (38) by an inner wall (54). Thereby, left chamber (36) with one such molecular sieve bed (52) contained therein may be maintained at one pressure, while the right chamber (38) with another such molecular sieve bed (52) contained therein may be maintained at another pressure. Each pump (40) has a pump inlet (56) and a pump outlet (58). The pump inlet (56) of the pressurization pump (40) is fluidly connected to the ambient air and configured to draw the ambient air into the remainder of the pressurization pump (40) and force the ambient air through the pump outlet (58) in fluid communication with the chamber inlet (50a). In the present example, each chamber inlet (50a) and each pump outlet (58) are essentially like structure. In another example, there may be less chamber inlets (50a), such as one chamber inlet (50a), fluidly connected to each pump outlet (58) by a manifold (not shown) for directing the ambient air into the chamber (36). Each chamber inlet (50a) further includes a pump particulate filter (60) configured to allow the flow of ambient air therethrough while inhibiting introduction of foreign debris into the gas concentration device (10) that may damage or reduce the efficiency of the gas concentration device (10) during use. The pump (40) also includes a desiccant (62) in one example configured to collect moisture from the ambient air prior to being introduced into the chambers (36, 38). The desiccant (62) improves the effectiveness of the process by reducing the moisture in the chambers (36, 38). Additional details regarding pump (40) as well as alternative pumps (210, 310) (see FIGS. 5-8) will be provided below. In any case, with respect to the present example, the plurality of pressurization and depressurization pumps (40) are all proximally positioned adjacent the chambers (36, 38) within the proximal housing portion (20) so as to be radially within an outer envelope (64) of chambers (36, 38) surrounding the longitudinal axis (45) and directly in the longitudinally proximal direction from the sieve beds (52) contained therein. Such arrangement directly proximal from the sieve beds (52) positions the pressurization and depressurization pumps (40) directly between the ambient air and the sieve beds (52) during use, but alternative arrangements with additional conduits may also be used. The invention is thus not intended to be unnecessarily limited to the particular arrangement of pressurization and depressurization pumps (40) shown in the present example.

The ambient air is pumped into the chambers (36, 38) and pressurized via the pressurization pumps (40) to the predetermined pressure. The predetermined pressure improves purity and adsorption capacity allowing for optimal mass transfer kinetics and regeneration. Once at the predetermined pressure, the molecular sieve bed (52) collects the processed gas and yields the enriched oxygen gas also contained within the chambers (36, 38). The phrase "collect" as used herein includes any method that separates a particular molecule from ambient air, such as by such as absorption and adsorption. Both the enriched oxygen gas as well as the processed gas are thus respectively purged from the chambers (36, 38) via the release outlets (51) and the chamber outlets (50b) as briefly discussed above. More particularly, the release outlets (51) are positioned in the distal housing portion (18) within a duct sidewall (66) of the breath duct (44) so as to fluidly connect the chambers (36, 38) to the breath duct (44) for the patient to inhale the enriched oxygen gas. A valve, such as a one-way valve (66), is positioned in each of the release outlets (51) and is configured to selectively vent the oxygen enriched gas from the chambers (36, 38) to the breath duct (44), while inhibiting backflow of fluid from the breath duct (44) into either of chambers (36, 38). For such selective venting, a vent actuator (70) is operatively connected to the one-way valve (66). The vent actuator (70) is configured to selectively open the one-way valve (66) to an open position for fluid communication from the chambers (36, 38) to the breath duct (44) as well as close the one-way valve (66) to a closed position to inhibit fluid communication from the chambers (36, 38) to the breath duct (44).

With respect to purging each of the chambers (36, 38) of the processed gas, chamber outlets (50) fluidly connect to depressurization pumps (50) configured to pump the processed gas from the sieve beds (52) within the chambers (36, 38) and back into the ambient environment outside of the nose (12) (see FIG. 1). Alternatively or in addition to purging the chamber outlets (50), gas concentration device (10) may further include another release outlet (72) positioned in the proximal housing portion (20) within the duct sidewall (66) of the breath duct (44) so as to fluidly connect the chambers (36, 38) to the breath duct (44). Another valve, such as another one-way valve (74), may be positioned in each of the release outlets (72) and configured to selectively vent the processed gas from the chambers (36, 38) to the breath duct (44), while inhibiting backflow of fluid from the breath duct (44) into either of chambers (36, 38). For such selective venting, another vent actuator (76) may be operatively connected to the one-way valve (74). The vent actuator (76) may be configured to selectively open the one-way valve (66) to an open position for fluid communication from the chambers (36, 38) to the breath duct (44) as well as close the one-way valve (66) to a closed position to inhibit fluid communication from the chambers (36, 38) to the breath duct (44). While blowdown of the processed gas occurs within the breath duct (44) as shown in one alternative example, valves (74) may be further configured to direct flow of processed gas during blowdown out of the proximal duct opening (48) and into the ambient environment. Purging chambers (36, 38) of the processed gas and the oxygen enriched gas through various release outlets (51, 72) and chamber outlets (50b) may result in at least some leakage of oxygen enriched gas through the release outlet (72) or the chamber outlet (50b) or at least some leakage of processed gas through release outlet (51). Such leakage may be acceptable in some examples so long the gas concentration device (10) provides sufficient oxygen enriched gas to the patient to improve patient outcome.

As briefly discussed above, the breath duct (44) longitudinally extends along the longitudinal axis (45) and is configured to receive vented oxygen enriched gas from the chambers (36, 38) for the patient to inhale. To this end, each breath duct (44) generally extends along an entire longitudinal length of left and right lateral housing bodies (22, 24) in order to fluidly connect the nasal vestibule (14) (see FIG. 1) to the ambient environment through the gas concentration device (10) to allow the patient to both inhale and exhale through the gas concentration device (10) during use. Each of the breath ducts (44) of the present example more particularly is centrally positioned in respective left and right lateral housing bodies (22, 24) such that chambers (36, 38) and pumps (40) radially surround breath ducts (44) within the respective outer envelopes (64) of left and right lateral housing bodies (22, 24). Furthermore, the distal and proximal duct openings (46, 48) of the present example further respectively include a distal duct filter (77) and a proximal duct filter (78) therein. Each of the distal and proximal duct filters (77, 78) are configured to allow the patient to inhale and exhale breath therethrough while inhibiting introduction of foreign debris into the breath duct (44) that may damage or reduce the efficiency of the gas concentration device (10) during use. In another example, alternative breath ducts configured to allow the patient to breath while the gas concentration device (10) is in the nose

(12) (see FIG. 1) of the patient may be positioned off of the longitudinal axis (45), such as along an outer surface of the housing (16). By way of further example, another alternative breath duct may be a channel open in the lateral direction to the nasal vestibule (14) (see FIG. 1) and/or the ambient environment. The invention is thus not intended to be unnecessarily limited to the particular breath duct (44) shown and described in the present example.

In order to enable controls and communication throughout the gas concentration device (10) during use, a computer arrangement (79) includes a left motherboard (80) operatively connected to a right mother board (82) respectively positioned within left and right lateral housing bodies (22, 24). Each of the motherboards (80, 82) has a central processing unit (CPU) and a wireless communicator, such as a BLUETOOTH® communicator, connected therein and configured to control operation of the pressurization and depressurization pumps (40) and the vent actuators (76) based on predetermined cycle operation discussed below in greater detail with feedback from one or more sensors, such as pressure sensors (84) and/or biosensors (86). In this respect the CPU is operatively connected to each of the pressurization and depressurization pumps (40), the vent actuators (76), the pressure sensors (84), and/or the biosensors (86) for communication therebetween. Each chamber (36, 38) of the present example includes at least one such pressure sensor (84) configured to detect a chamber pressure and communicate the chamber pressure to the CPU in real time. One example further includes the biosensors (86) configured to detect a measurable condition of the patient and communicate the measurable condition, such as the blood oxygen level, $SpO^2$, respiratory rate, heart rate, irregular heart rhythms, and fall detection to the CPU in real time. A biosensor (86) to detect irregular heart rhythms may be detected by an optical heart sensor, pulse oximeter, or an electrical heart sensor. A biosensor (56) that detects a fall may be detected by an accelerometer and a gyroscope. Biosensors (86) of the present example are positioned in the distal housing portion (18), although it will be appreciated that such biosensors (86) may be in any such position to detect the measurable condition about the housing (16) within the nasal vestibule (14) (see FIG. 1).

As discussed briefly above, the connection bridge (26) laterally extends between the left and right lateral housing bodies (22, 24) to maintain the gap (28) configured to receive the nasal cartilage (30) (see FIG. 1). during use. More particularly, the connection bridge (26) of the present example is removably connected to each of the left and right lateral housing bodies (22, 24) and includes a left removal button (88) and a right removal button (90). Each of the left and right removal buttons (88, 90) is configured to be depressed by the patient to thereby disconnect the respective left and right lateral housing bodies (22, 24) from the connection bridge (26). The connection bridge (26) of the present example is rigid enough to maintain the gap (28), but resiliently biased to grip the nasal cartilage (30) (see FIG. 1) between the left and right lateral housing bodies (22, 24). Connection bridge (26) includes an atraumatic pad (27) configured to engage the nasal cartilage (see FIG. 1) without damaging the nasal cartilage (see FIG. 1) during use. In one or more examples, the atraumatic pad (27) may be constructed of foam, silicone, and/or rubber. In any case, it will be appreciated that the atraumatic pad (27) may be any material suitable material for enhancing the comfort of the connection bridge (26) on the nasal cartilage (30) without damaging the nasal cartilage (30) (see FIG. 1).

The gas concentration device (10) further includes at least one device battery (92), which, in one example, is incorporated into the connection bridge (26). More particularly, the device battery (92) forms a portion of the connection bridge (26), such as by additive manufacturing with known materials configured to store and release electrical energy. Alternatively or in addition, such device battery (92) may be further incorporated into the left and right lateral housing bodies (22, 24) for additional electrical energy storage capacity. In still other examples, alternative batteries may be removable and/or traditional storage batteries, such as a button cell, lithium ion battery. In any case, the device battery (92) is operatively connected to the pumps (40), the vent actuators (70, 76), the computer arrangement (79), including the motherboards (82, 84), the pressure sensors (84), and the biosensors (86), and any other electrical components of gas concentration device (10) for powering during use. The gas concentration device (10) further includes distal and proximal annular charging plates (94, 96) respectively positioned on distal and proximal housing portions surrounding distal and proximal duct openings (46, 48). The distal and proximal annular charging plates (94, 96) in one example are operatively connected to the device battery (92) in order to communicate electrical power from an electrical charger, such as a charging case (610) (see FIG. 13A) discussed below in greater detail. Additional charging plates (not shown) may be incorporated between the connection bridge (26) and the left and right lateral housing bodies (22, 24) to removably electrically connect the connection bridge (26) to the left and right lateral housing bodies (22, 24) according to another example.

As will be discussed below in greater detail during use, chambers (36, 38) of each of the left and right lateral housing bodies (22, 24) are generally fluidly sealed from each other despite selectively opening to receive ambient air or purge the processed gas and the oxygen enriched gas. Still, in one example, gas concentration device (10) includes additional valves (100, 104) and conduits (98, 102) configured to fluidly connect two or more of the chambers (36, 38) in use. By way of further example, FIGS. 2-4 show a connection conduit (98) extending between two connection valves (100) respectively positioned in the left and right lateral housing bodies (22, 24). The left connection valve (100) is fluidly connected between the right chamber (38) of the left lateral housing body (22) and conduit (98), whereas the right connection valve (100) is fluidly connected between the left chamber (36) of the right lateral housing body (24) and conduit (98). Such connection valves (100) are generally closed in a closed position to fluidly isolate the left and right lateral housing bodies (22, 24), but may be opened to an open position to fluidly communicate between the left and right lateral housing bodies (22, 24) through the connection conduit (98) in some instances. Similarly, a pair of crossover conduits (102) with a pair of crossover valves (104) therein are positioned in each inner wall (54) between chambers (36, 38) of both of the left and right lateral housing bodies (22, 24). Such crossover valves (104) are generally closed in a closed position to fluidly isolate the left and right chambers (36, 38), but may be opened to an open position to fluidly communicate between the left and right chambers (36, 38) through the crossover conduits (98) in some instances. In an example incorporating each of the valves (100, 104) and the conduits (98, 102), fluid communication may occur between all of the chambers (36, 38) of gas concentration device (10) as desired. Of course, such valves (100, 104) and the conduits (98, 102) are merely optional and not intended to unnecessarily limit the invention shown and described herein.

In use, with respect to FIGS. 1-4, the patient inserts the left and right lateral housing bodies (22, 24) of the gas concentration device (10) respectively into the left and right nostrils (32, 34) such that the nasal cartilage (30) is received within the gap (28) and against the connection bridge (26). The left and right lateral housing bodies (22, 24) are generally cylindrical with a domed distal housing portion (18) on each of the left and right lateral housing bodies (22, 24). Such left and right lateral housing bodies (22, 24) are further sized to engage against the nose (12) within the nasal vestibule (14) to removably secure the gas concentration device (10) within the nose (12). In one example, at least a portion of the sieve beds (52) is positioned within the nasal vestibule (14) while contained within the chambers (36, 38), although the invention is not intended to be unnecessarily limited to such placement of the sieve beds (52) within the nose (12).

Once sufficiently secured in the nose (12), the CPU of the computer arrangement (79) directs pressurization pumps (40) fluidly connected to the left chambers (36) in each of the left and right lateral housing bodies (22, 24) to pump ambient air into the left chambers (36) during an absorption cycle. From 1 atmosphere of pressure (ATM) within the left chambers (36), the pressurization pumps (40) continue to pump the ambient air until to the predetermined pressure at which the sieve beds (52) adsorb the processed gas, including nitrogen, separated from the oxygen enriched gas. In one example of the adsorption cycle, the predetermined pressure is between approximately 1 ATM and approximately 4 ATM or, more particularly, between approximately 2 ATM and approximately 3 ATM or, still more particularly at approximately 2.5 ATM, and the approximate time to increase to the predetermined pressure is approximately 1 second. The ratio of adsorption pressure to desorption pressure should be roughly a 3:1 ratio. Once the pressure sensors (84) in the left chambers (36) detect and communicate the predetermined pressure to the CPU, the CPU of the computer arrangement (79) fluidly seals the left chambers (36) and halts the pressurization pumps (40) to complete absorption of the processed gas within the sieves beds (52).

The CPU of the computer arrangement (79) then selectively actuates the vent actuators (70) associated with each of the left chambers (36) to open both of the release outlets (51) via the one-way valves (66) during a blowdown cycle. The oxygen enriched gas initially purges from the release outlets (51) at the predetermined pressure into the breath ducts (44). As the predetermined pressure decreases, slowing the flow of the oxygen enriched gas into the breath ducts (44), the CPU of the computer arrangement (79) directs the depressurization pumps (40) fluidly connected to the left chamber (36) in each of the left and right lateral housing bodies (22, 24) to pump the processed gas from the sieve beds (52) and into the ambient environment. Once an available amount of the oxygen enriched gas is purged into the breath ducts (44), the CPU of the computer arrangement (79) selectively actuates the vent actuators (70) associated with each of the left chambers (36) to close both of the release outlets (51) via the one-way valves (66) and terminate flow therethrough. The depressurization pumps (40) associated with the left chambers (36) continue to purge the processed gas from the sieve beds (51) and, in one example, generates a vacuum in the left chambers (36) until the processed gas is sufficiently purged therefrom sensed by the pressure sensors (84), thereby completing the blowdown cycle. In another example, the depressurization pumps (40) associated with the left chambers (36) continue to purge the processed gas from the sieve beds (51) and, in one example, generates a vacuum in the left chambers (36) until the processed gas is sufficiently purged therefrom sensed by the pressure sensors (84), thereby completing the blowdown cycle.

In yet another example, processed gas from the left chamber (36) can be used to pressurize the right chamber (38) during the pressurization of the molecular sieve bed (52) in the right chamber (38) through the valve (102, 104) during the blowdown phase. This will allow for pressurization to reach optimal adsorption pressure and increase enriched gas purification while simultaneously depressurizing the left chamber (36). The reverse of this process also occurs during the depressurization of the right chamber (38) to assist in pressurizing the left chamber (36). In one example, the blowdown cycle takes approximately 2 seconds. In another example, the blowdown cycle may take less than 2 seconds. In yet another example, the blowdown cycle may take less than a second.

While the left chambers (36) and associated pumps (40) were completing the blowdown cycle in the present example, the CPU of the computer arrangement (79) simultaneously directs the pressurization pumps (40) fluidly connected to the right chamber (38) in each of the left and right lateral housing bodies (22, 24) to pump ambient air into the right chambers (38) during another absorption cycle. Once the absorption cycle in each of the right chambers (38) is completed similar to the left chambers (36) discussed above, the CPU of the computer arrangement (79) initiates the blowdown cycles in each of the right chambers (38) followed by repeating the absorption cycles in the left chambers (36). The absorption and blowdown cycles are thus staggered between the left chambers (36) and the right chambers (38) to generate sufficient oxygen enriched gas within the nasal vestibule (14) so that the patient can breathe with increased comfort. Throughout these cycles, the patient periodically inhales through the breath duct (44) to breath in the oxygen enriched gas as well as exhales through the breath duct (44) as desired. Furthermore, the patient may remove the gas concentration device (10) from the nose (12) as desired, such as for charging, which is discussed below in greater detail.

While the above description staggers the above cycles in left chambers (36) of the left and right lateral housing bodies (22, 24) relative to the right chambers (36) of the left and right lateral housing bodies (22, 24), it will be appreciated that the pressurization and blowdown cycles may occur in the chambers (36, 38) in any desired pattern and rate for generating the oxygen enriched gas for the patient to inhale. Similarly, the above referenced pressures and times are merely exemplary and not intended to unnecessarily limit the invention. It will be appreciated that any pressure and times configured to generate sufficient oxygen enriched gas to enhance the patient outcomes may be similarly used.

II. EXEMPLARY PUMPS FOR GAS CONCENTRATION DEVICE

Figure 5:
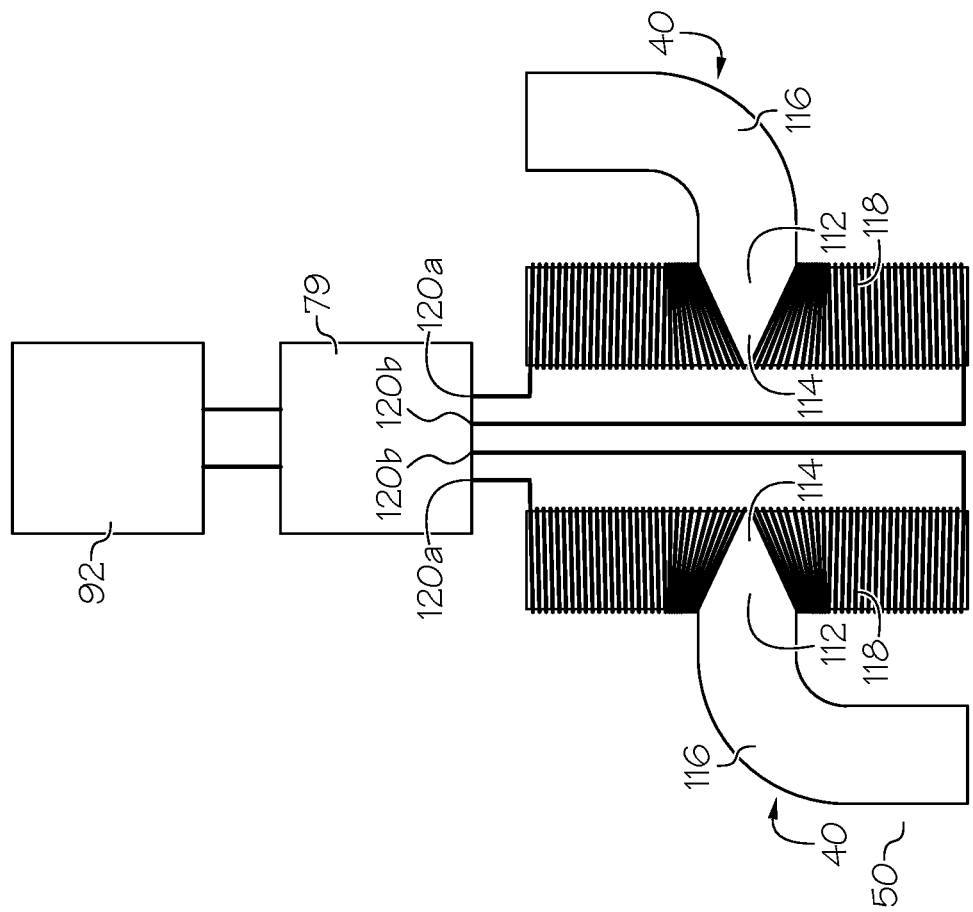
FIG. 5 depicts a schematic, side elevational view of a first example of a pressurization pump and a depressurization pump.

In one example of the gas concentration device (10) discussed above in greater detail, pressurization and depressurization pumps (40) are configured to pump ambient air into the chambers (36, 38) as well as purge the processed gas from the chambers (36, 38), in one example of gas concentration device (10) discussed above in greater detail. To this end, FIGS. 5 and 6A-6E show a first example of a pump (40)

in greater detail that may be incorporated into the gas concentration device (10). The pressurization pump (40) and the depressurization pump (40) shown in FIG. 5 are each identical, but for the orientation relative to the chambers (36, 38) (see FIGS. 3-4) for pumping ambient air into the chambers (36, 38) or processed gas from the chambers (36, 38) (see FIGS. 3-4). As shown in the present example, the left pump (40) of FIG. 5 is the depressurization pump (40), whereas the right pump (40) is the pressurization pump (40), although it will be appreciated that any arrangement of pumps (40) may be similarly used.

With respect to FIGS. 5 and 6A, pump (40) of the present example includes a pump housing (112) having a piston chamber (114), a pump duct (116) extending from and fluidly connected to the piston chamber (114), and a coil (118), such as a metallic coil such as a copper wire coil, wrapped around an outer surface of the piston chamber (114). In one example, a superconductor may be used to generate a strong current/magnetic field around the coils. A piston member, such as a piston ball (119), is received within the piston chamber (114) configured to selectively reciprocate in the longitudinal direction for pumping fluid through the pump duct (116) as discussed below in greater detail. The piston ball (119) may be constructed of ferrous materials. The piston chamber (114) and the pump duct (116) may be also a filter (not shown) or mesh (not shown) between piston chamber (114) and (116) to keep piston ball (119) within the piston chamber (114).

The device battery (92) and the computer arrangement (79) are each connected to opposing distal and proximal coil ends (120a, 120b) and configured to selectively direct the reciprocation in either the distal direction or the proximal direction based on the directional flow of current through the coil (118) from the device battery (92) as directed by the computer arrangement (79). More particularly, in the present example, the computer arrangement (79) initiates flow from the distal coil end (120a) toward the proximal coil end (120b) to generate a magnetic field within the piston chamber (114) that forces the piston ball (119) in the proximal direction. In contrast, the computer arrangement (79) initiates flow from the proximal coil end (120b) toward the distal coil end (120a) to generate a magnetic field within the piston chamber (114) that forces the piston ball (119) in the distal direction. Piston ball (119) is sized to generate at least a partial seal against an inner surface of the piston chamber (114) in use. While the piston ball (119) as shown in the present example is spherical in shape, it will be appreciated that a piston member may be any alternative size or shape configured to reciprocate within the piston chamber (114). The invention is thus not intended to be limited to the particular piston ball (119) of the present example.

Furthermore, fluid flow through the pump (40) is also controlled by a plurality of valves (122, 124, 126) fluidly connected within pump housing (112) as shown in FIG. 6A. More particularly, the valves (122, 124, 126) in one example include a chamber valve (122) positioned within the piston chamber (114) adjacent to the pump inlet (56), a duct valve (124) positioned within the pump duct (116) adjacent to the pump outlet (58), and a vent valve (126) positioned within the piston chamber (114) longitudinally opposite from the pump inlet (56). The chamber valve (122) is resiliently biased closed in a closed position and configured to inhibit backflow toward the pump inlet (56), but is drawn open to an open position in the presence of a vacuum within the piston chamber (114) so as to draw fluid through the chamber valve (122). However, the chamber valve (122) permits at least some leakage toward the pump inlet (56) in order to prevent hydrostatic locking of the piston ball (119) and accommodate seating of the piston ball (119) toward to the pump inlet (56). The duct valve (124) similarly is resiliently biased closed in a closed position and configured to inhibit backflow from the pump outlet (58), but is forced open to an open position in the presence of a pressure within the pump duct (116) such that pressurized fluid flows through the duct valve (124) and out of the pump outlet (58). In addition, the vent valve (126) is generally closed in a closed position, but configured to permit at least some leakage from the piston chamber (114) in order to accommodate seating of the piston ball (119) at the distal end of piston chamber (114) away from the pump inlet (56).

In use, FIGS. 5-6E show the computer arrangement (79) directing electrical power from the device battery (92) in order to perform a vacuum stroke and a pressure stroke of the pump (40). With respect to FIG. 6A, piston ball (119) seats against a first seat (128) in an initial position of the vacuum stroke of the pressure cycle. The magnetic field forces the piston ball (119) from the first seat (128) distally through the piston chamber (114) and, in turn, draws the fluid, such as the ambient air, into the piston chamber (114). The piston ball (119) continues distally moving through the piston chamber (114) to a mid-proximal position as shown in FIG. 6B with the piston ball (119) aligned with a proximal edge of the pump duct (116) and forcing excess fluid under pressure through the duct valve (124). As the piston ball (119) distally moves from the mid-proximal position to the mid-distal position shown in FIG. 6C, a vacuum is drawn in the pump duct (116) that closes the duct valve (124) while fluid, such as the ambient air, continues to be drawn into the piston chamber (114) and is introduced into the pump duct (116). With respect to FIGS. 6C and 6D, the piston ball (119) completes the vacuum stroke in a terminal position of the vacuum stroke upon seating against second seat (130) and terminating additional draw of the fluid through the chamber valve (122) adjacent to the pump inlet (56). In the present example, the vent valve (126) opens once the fluid seal around the piston ball (119) passes the mid-distal position in order to inhibit a hydrostatic lock of the piston ball (119) between the piston ball (119) and the second seat (130) until the piston ball (119) is seated in the terminal position of the vacuum stroke.

The terminal position of the vacuum stroke, in turn, becomes an initial position of the pressure stroke as the magnetic field reverses to force the piston ball (119) from the second seat (130) back toward the first seat (128) as shown in FIG. 6D, closing chamber valve (122). The proximal movement of the piston ball (119) during the pressure stroke pressurizes the fluid within the piston chamber (114) and the pump duct (116) in order force the fluid, such as the ambient air, against the duct valve (124), thereby opening the duct valve (124) and discharging the fluid from the pump outlet (58). Such discharge continues as the piston ball (119) passes proximally by the mid-distal position shown in FIG. 6E and beyond the mid-proximal position to the terminal position of the pressure stroke, which again becomes the initial position of the vacuum stroke to be continually repeated as desired. In the present example, the chamber valve (122) leaks once the fluid seal around the piston ball (119) passes the mid-proximal position in order to inhibit a hydrostatic lock of the piston ball (119) between the piston ball (119) and the first seat (128) until the piston ball (119) is seated in the terminal position of the pressure stroke.

FIGS. 7A-7E show a second example of a pump (210) that may be incorporated into the gas concentration device (10) as the pressurization or depressurization pump (210).

The pump (210) of the present example is similar to the pump (40) (see FIG. 6A) discussed above, but replaces the piston ball (119) (see FIG. 6A) with an undersized piston ball (219) such that the pump (210) does not include the vent valve (126) (see FIG. 6A). This pump (210) also may have a filter (not shown) or mesh (not shown) between piston chamber (114) and (116) to keep piston ball (119) within the piston chamber (114). In other respects, the pump (210) is similar to the pump (40) such that like numbers discussed below and shown in the figures indicate like features discussed above.

In use, FIGS. 7A-7E show the computer arrangement (79) (see FIG. 5) directing electrical power from the device battery (92) (see FIG. 5) in order to perform a vacuum stroke and a pressure stroke of the pump (210). With respect to FIG. 7A, the undersized piston ball (219) seats against the first seat (128) in the initial position of the vacuum stroke of the pressure cycle. The magnetic field forces the undersized piston ball (219) from the first seat (128) distally through the piston chamber (114) and, in turn, draws the fluid, such as the ambient air, into the piston chamber (114). The undersized piston ball (219) continues distally moving through the piston chamber (114) to a mid-proximal position as shown in FIG. 7B with the undersized piston ball (219) aligned with a proximal edge of the pump duct (116) and forcing excess fluid under pressure through the duct valve (124). As the undersized piston ball (219) distally moves from the mid-proximal position to the mid-distal position shown in FIG. 7C, a vacuum is drawn in the pump duct (116) that closes the duct valve (124) while fluid, such as the ambient air, continues to be drawn into the piston chamber (114) and is introduced into the pump duct (116). With respect to FIGS. 7C and 7D, the undersized piston ball (219) completes the vacuum stroke in the terminal position of the vacuum stroke upon seating against second seat (130) and terminating additional draw of the fluid through the chamber valve (122) adjacent to the pump inlet (56). In the present example, the fluid leaks around the undersized piston ball (219) through an annular gap (232) between the undersized piston ball (219) and the inner surface of the piston chamber (114). The annular gap (232) is thus small enough to provide sufficient fluid seal to generate pressure and/or vacuum during use, but large enough to allow sufficient leakage to inhibit a hydrostatic lock of the undersized piston ball (219) between the piston ball (219) and the second seat (130) as the undersized piston ball (219) seats in the terminal position of the vacuum stroke.

The terminal position of the vacuum stroke, in turn, becomes the initial position of the pressure stroke as the magnetic field reverses to force the undersized piston ball (219) from the second seat (130) back toward the first seat (128) as shown in FIG. 7D, closing chamber valve (122). The proximal movement of the undersized piston ball (219) during the pressure stroke pressurizes the fluid within the piston chamber (114) and the pump duct (116) in order force the fluid, such as the ambient air, against the duct valve (124), thereby opening the duct valve (124) and discharging the fluid from the pump outlet (58). Such discharge continues as the undersized piston ball (219) passes proximally by the mid-distal position shown in FIG. 7E and beyond the mid-proximal position to the terminal position of the pressure stroke, which again becomes the initial position of the vacuum stroke to be continually repeated as desired. In the present example, leakage through the annular gap (232) around the undersized piston ball (219) as the undersized piston ball (219) passes the mid-proximal position inhibits a hydrostatic lock of the undersized piston ball (119) between the piston ball (119) and the first seat (130) as the piston ball (119) seats in the terminal position of the pressure stroke.

While the above descriptions of the pressure cycle of pumps (40, 210) are generally described with respect to the pressurization pumps (40, 210), it will be appreciated that above referenced proximal and distal movements are simply reversed for the depressurization pump (40, 210) as arranged in the present example of the gas concentration device (10) (see FIGS. 2-4). The pressurization and depressurization pumps (40, 210) are alike in all other respects unless otherwise noted herein.

Figure 8:
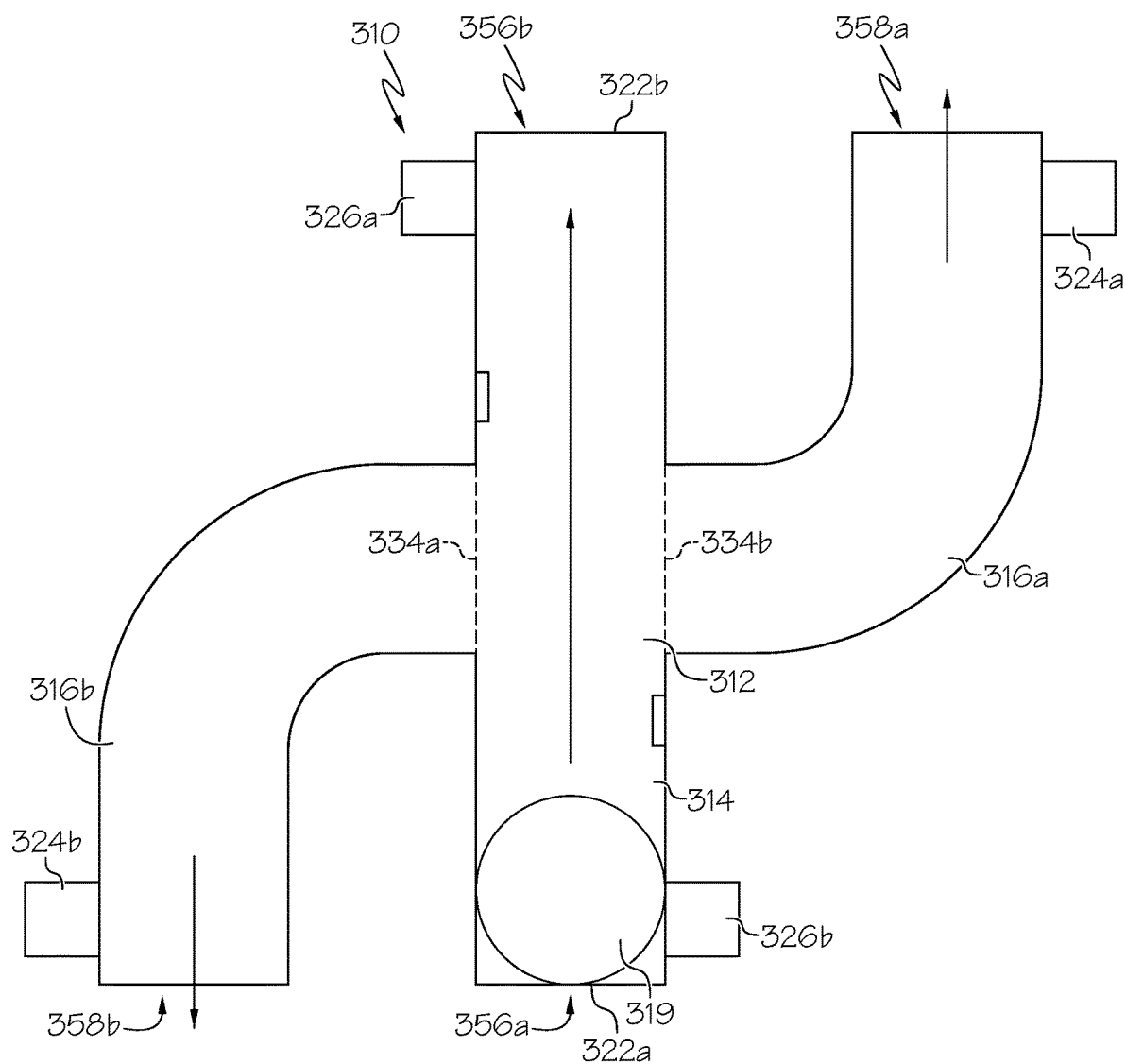
FIG. 8 depicts a schematic, side elevational view of a dual pressurization pump.
Figure 9A:
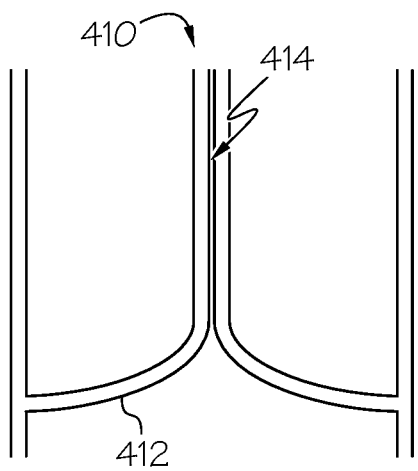
FIG. 9A depicts a schematic sectional view of a bicuspid valve in a closed position.
Figure 9B:
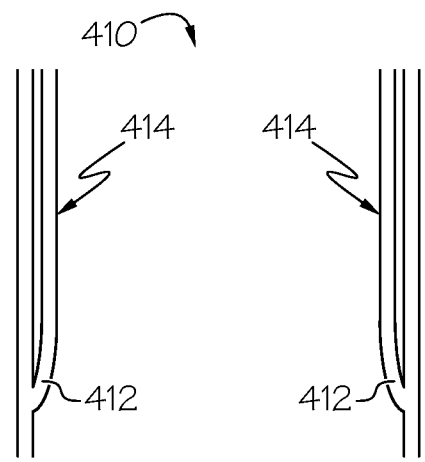
FIG. 9B depicts the schematic sectional view of the bicuspid valve similar to FIG. 9A, but with the bicuspid valve in an open position.

FIG. 8 shows a third example of pump (310) referred to herein as a dual pressurization pump (310). The dual pressurization pump (310) is configured to pressurize and depressurize chambers (36, 38) (see FIG. 2) in respective pressurization and depressurization modes from a single orientation. The dual pressurization pump (310) of the present example includes a pump housing (312) having a piston chamber (314), a distal pump duct (316a) distally extending from and fluidly connected to the piston chamber (314), a proximal pump duct (316b) proximally extending from and fluidly connected to the piston chamber (314) and a coil (not shown), such as a metallic coil, wrapped around an outer surface of the piston chamber (314). A piston member, such as a piston ball (319), is received within the piston chamber (314) configured to selectively reciprocate in the longitudinal direction for pumping fluid through the distal and proximal pump ducts (316) as discussed below in greater detail. The device battery (92) (see FIG. 5) and the computer arrangement (79) (see FIG. 5) are each connected to opposing distal and proximal coil ends (not shown) and configured to selectively direct the reciprocation in either the distal direction or the proximal direction based on the directional flow of current through the coil (not shown) like pump (40) (see FIG. 5) discussed above in greater detail. The piston ball (319) is sized to generate at least a partial seal against an inner surface of the piston chamber (314) in use. While the piston ball (319) as shown in the present example is spherical in shape, it will be appreciated that a piston member may be any alternative size or shape configured to reciprocate within the piston chamber (314). The invention is thus not intended to be limited to the particular piston ball (319) of the present example.

Furthermore, fluid flow through the dual pressurization pump (310) is also controlled by a plurality of valves (322a, 322b, 324a, 324b, 326a, 326b, 334a, 334b) fluidly connected within pump housing (312) as shown in FIG. 8. More particularly, the valves (322a, 322b, 324a, 324b) in one example include proximal and distal chamber valves (322a, 322b) positioned within the piston chamber (314) respectively adjacent to proximal and distal pump inlets (356a, 356b) and distal and proximal duct valves (324a, 324b) positioned respectively within the distal and proximal pump ducts (316a, 316b) adjacent to distal and proximal pump outlets (358a, 358b). In addition, valves (326a, 326b, 334a, 334b) include distal and proximal vent valves (326a, 326b) positioned within the piston chamber (114) respectively longitudinally opposite from the proximal and distal pump inlets (356b, 356a) as well as pressurization and depressurization state valves (334a, 334b) respectively positioned where the proximal and distal pump ducts (316b, 316a) intersect and fluidly connect with the piston chamber (314). The proximal and distal chamber valves (322a, 322b) are each resiliently biased closed in a closed position and configured to inhibit backflow toward the respective proximal and distal pump inlets (356a, 356b), but are drawn open to an open position in the presence of a vacuum within the piston chamber (314) so as to draw fluid through the proximal and distal chamber valves (322a, 322b). However, the proximal and distal chamber valves (322a, 322b) permit at least some leakage toward the proximal and distal pump inlets (356a, 356b) in order to accommodate seating of the piston ball (319) toward to the proximal and distal pump inlets (356a, 356b).

The distal and proximal duct valves (324a, 324b) similarly are resiliently biased closed in a closed position and configured to inhibit backflow from the distal and proximal pump outlets (358a, 358b), but are forced open to an open position in the presence of a pressure respectively within the distal and proximal pump ducts (316a, 316b) such that pressurized fluid respectively flows through the distal and proximal duct valves (324a, 324b) and out of the distal and proximal pump outlets (358a, 358b). In addition, the distal and proximal vent valves (326a, 326b) are generally closed in a closed position, but configured to permit at least some leakage from the piston chamber (314) in order to accommodate seating of the piston ball (319) respectively away from the distal and proximal pump inlets (356a, 356b).

The pressurization and depressurization state valves (334a, 334b) are configured to open or close according to a pressurization mode in which the dual pressurization pump (310) pressurizes the chambers (36, 38) (see FIG. 2) for the absorption cycle and the depressurization mode in which the dual pressurization pump (310) depressurizes the chambers (36, 38) (see FIG. 2) for the blowdown cycle. In the pressurization mode, the pressurization state valve (334a) is closed in a closed position and the depressurization valve is open in an open position. During the pressurization mode, the piston chamber (314), the piston ball (319), the distal pump duct (316a), the proximal chamber valve (322b), the distal duct valve (324a), and the distal vent valve (326a) respectively operate in use like the piston chamber (114) (see FIG. 6A), the piston ball (119) (see FIG. 6A), the pump duct (116) (see FIG. 6A), the chamber valve (122) (see FIG. 6A), the duct valve (124) (see FIG. 6A), and the distal vent valve (126) (see FIG. 6A) as discussed above to pressurize the chambers (36, 38) (see FIG. 2). In contrast, during the depressurization mode, the piston chamber (314), the piston ball (319), the proximal pump duct (316b), the distal chamber valve (322b), the proximal duct valve (324b), and the proximal vent valve (326b) respectively operate in use like the piston chamber (114) (see FIG. 6A), the piston ball (119) (see FIG. 6A), the pump duct (116) (see FIG. 6A), the chamber valve (122) (see FIG. 6A), the duct valve (124) (see FIG. 6A), and the distal vent valve (126) (see FIG. 6A) as discussed above to depressurize the chambers (36, 38) (see FIG. 2). In this respect, the same piston chamber (314) and the same piston ball (319) are used in each of the pressurization and depressurization modes in the same orientation relative to the chambers (36, 38) (see FIG. 2). In one example, the computer arrangement (79) (see FIG. 5) is operatively connected to the plurality of valves (322a, 322b, 324a, 324b, 326a, 326b, 334a, 334b) to direct the flow of fluids, such as the ambient air or the processed gas, during use.

FIGS. 9A-12B show a bicuspid valve (410) and a tricuspid valve (510) that may be used as one or more of valves (122, 124, 322a, 322b, 324a, 324b) (see FIGS. 6A-8) in one or more examples. In the present example, duct valves (124, 324a, 324b) (see FIGS. 6A-8) are each the bicuspid valve (410), whereas the chamber valves (122, 322a, 322b) (see FIGS. 6A-8) are each the tricuspid valve (510). Tricuspid valves (510) generally provides additional leakage as compared to the bicuspid valve (510). Such additional leakage may further reduce the likelihood of hydrostatic lock of as piston ball (119, 319) (see FIGS. 6A-8) approaches the tricuspid valve (510) during use as discussed above in greater detail. Alternative valves may also be used in place of one or more (122, 124, 322a, 322b, 324a, 324b) such that the invention is not intended to be unnecessarily limited to the particular bicuspid or tricuspid valves (410, 510) shown and described in the present example.

Figure 10A:
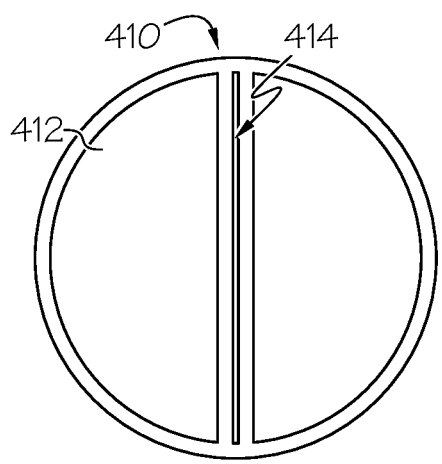
FIG. 10A depicts a schematic end view of the bicuspid valve of FIG. 9A in the closed position.
Figure 10B:
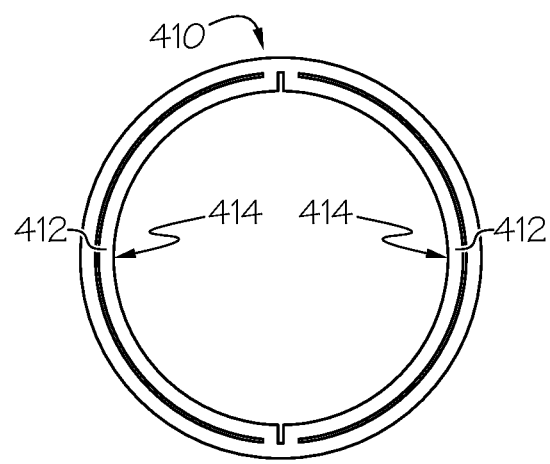
FIG. 10B depicts the schematic end view of the bicuspid valve similar to FIG. 10A, but with the bicuspid valve in the open position.

With respect to FIGS. 9A-10B, the bicuspid valve (410) includes one or more leaflets (412) having one or more sealing surfaces (414). In the current example, bicuspid valve (410) includes two leaflets (412) having one sealing surface (414) on each leaflet (412). The leaflets (412) may be constructed from any suitable material known in the art that has sufficiently rigid, yet flexible properties. The bicuspid valve (410) has an open position and a closed position. In the closed position shown in FIGS. 9A and 10A, the leaflets (412) are resiliently biased closed in a closed position. The leaflets (412) are configured to tightly seal against each other along the sealing surface (414). The sealing surface (414) inhibits fluid backflow in the closed position. FIGS. 9B and 10B shows bicuspid valve (410) in the open position.

The leaflets (412) are transitioned between the open and closed positions by a pressure differential across the bicuspid valve (410). When pressure above the bicuspid valve (410) is higher than the pressure below the bicuspid valve (410), the leaflets (412) are urged towards each other and the sealing surfaces (414) act upon each other to create a fluid tight seal, shown in FIGS. 9A and 10A. Alternatively, when the pressure below the bicuspid valve (410) is higher than the pressure above the bicuspid valve (410), the bicuspid valve is urged towards the open position, shown in FIGS. 9B and 10B.

With respect to FIGS. 11A-12B, the tricuspid valve (510) includes one or more leaflets (512) having one or more sealing surfaces (514). In the current example, the tricuspid valve (510) includes three leaflets (512) having two sealing surfaces (514) on each leaflet (512). The tricuspid valve (510) is constructed, configured, and operates similarly to bicuspid valve (410). The tricuspid valve (510) also uses pressure differential across the tricuspid valve (510) to transition between the open and closed positions. However, the tricuspid valve (510) differs from the bicuspid valve (410) in that the sealing surfaces (514) allow for additional fluid leakage in the closed position. Such additional leakage may further reduce the likelihood of hydrostatic lock of as the piston ball (119, 319) (see FIGS. 6A-8) approaches the tricuspid valve (510) during use as discussed above in greater detail. The tricuspid valve is shown in the closed position in FIGS. 11A and 12A. The tricuspid valve is shown in the open position in FIGS. 11B and 12 B.

III. EXEMPLARY CHARGING CASE FOR GAS CONCENTRATION DEVICE

Figure 13A:
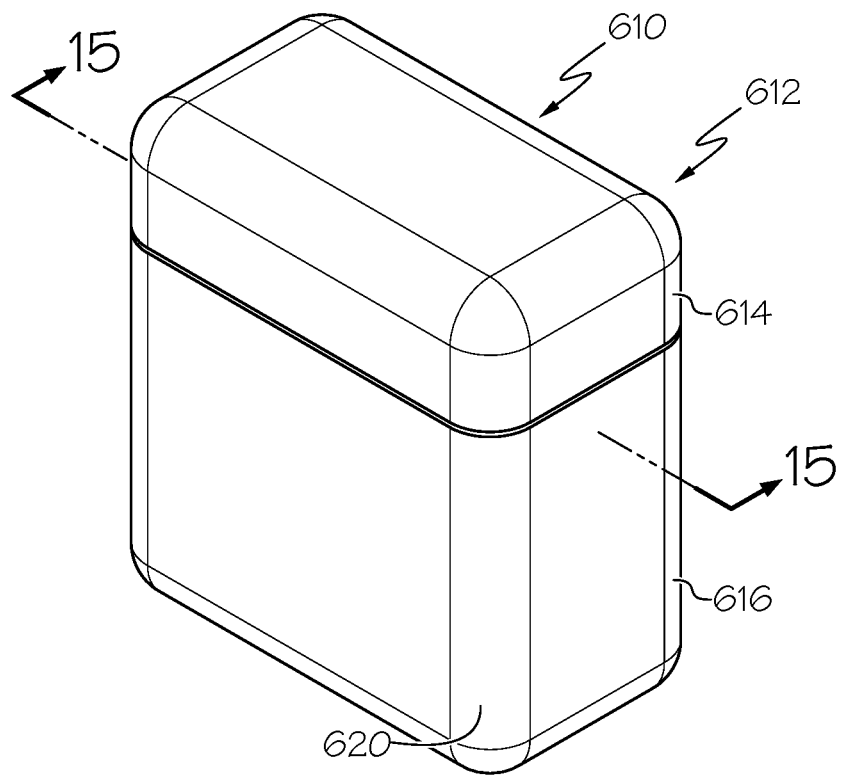
FIG. 13A depicts a perspective view of a charging case for the gas concentration device of FIG. 1 with a lid in a closed position configured to contain the gas concentration device while charging.
Figure 13B:
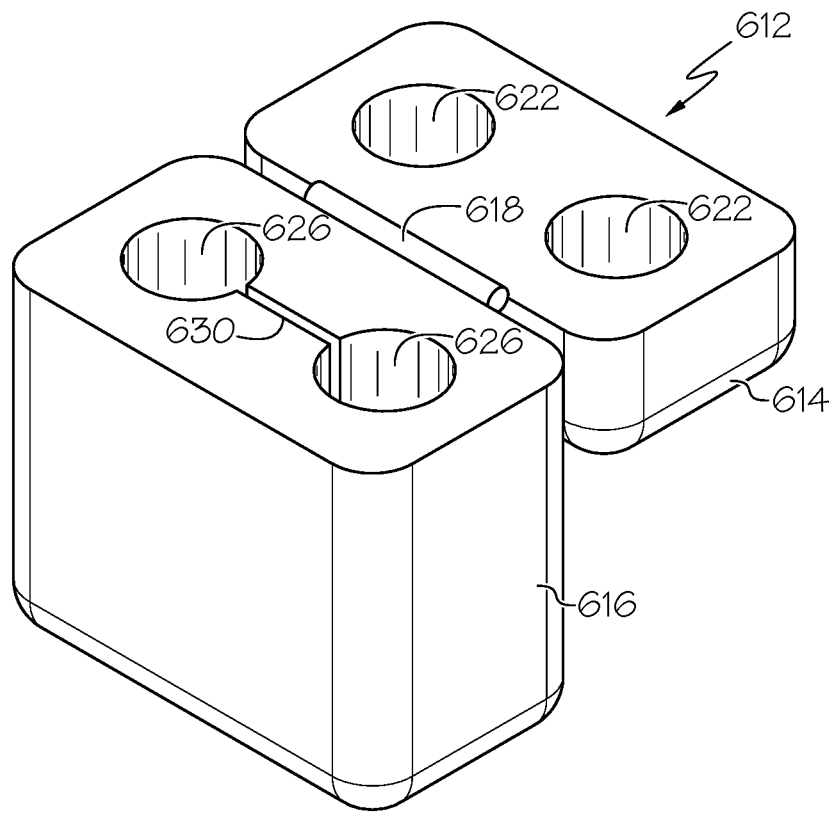
FIG. 13B depicts the perspective view of the charging case similar to FIG. 13A, but showing the lid in an open position for receiving or removing the gas concentration device of FIG. 1.
Figure 14:
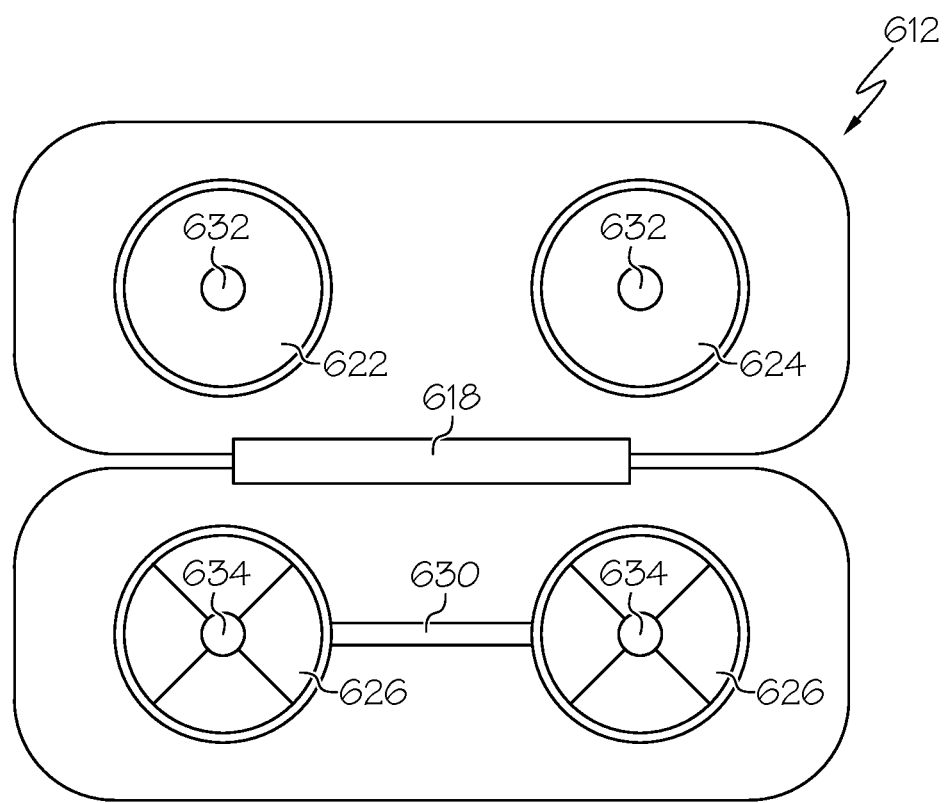
FIG. 14 depicts a top view of the charging case of FIG. 13B with the lid in the open position.
Figure 15:
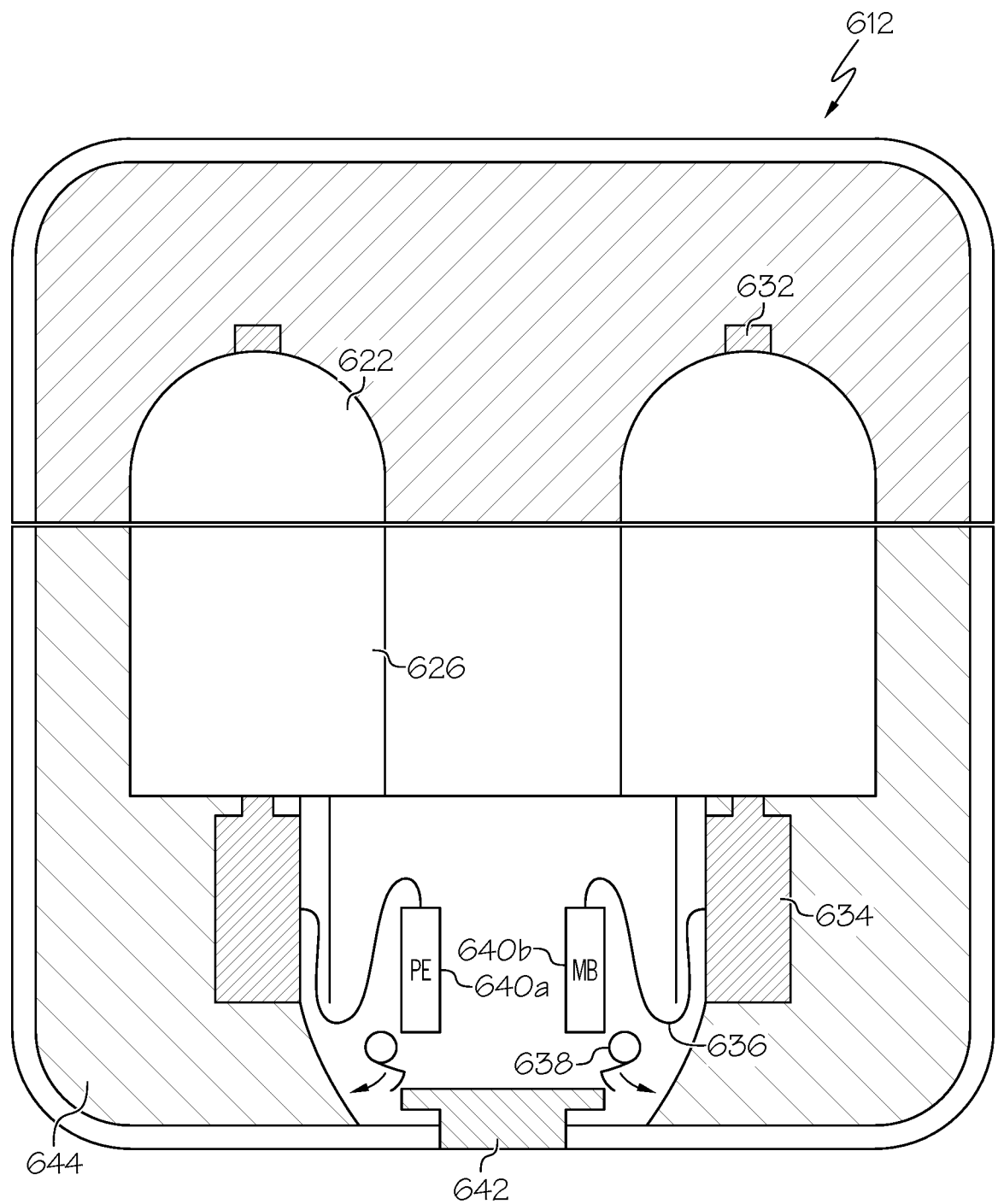
FIG. 15 depicts a cross-sectional view of the charging case of FIG. 13A taken along section line 15-15.

A system (610) for providing the enriched gas, such as the oxygen enriched gas, is shown in FIG. 13A and includes the gas concentration device (10) (see FIG. 1) and a charging case (612). With respect to FIG. 2 and FIGS. 13A-15, the charging case (612) is configured to retain the gas concentration device (10), charge the device battery (92), and charge a case battery (644). The charging case (612) is generally rectangular in shape, having a chamfered edge (620). The charging case (612) has an open position and a closed position. FIG. 13A shows the charging case (612) in the closed position, whereas FIG. 13B shows the charging case (612) in the open position.

The charging case (612) includes a lid (614), a case housing (616), and a hinge (618). The lid (614) has a distal left bore (622) and a distal right bore (624). The distal left bore (622) is configured to receive the distal housing portion (18) of the left lateral housing body (22) while the distal right bore (624) is configured to receive the distal housing portion (18) of the right lateral housing body (24). The lid (618) is distally located relative to the remainder of the case housing (616) and is hingedly connected to the case housing (616) by the hinge (618). The hinge (618) may further include a spring (not shown) to urge the lid (614) toward the closed position.

The case housing (616) has a proximal left bore (626), a proximal right bore (628), and a bridge slot (630). The proximal left bore (626) is configured to receive the proximal housing portion (20) of the left lateral housing body (22), and the proximal right bore (628) is configured to accept the proximal housing portion (20) of the right lateral housing body (24). The bridge slot (630) extends between the proximal left bore (626) and the proximal right bore (628). The bridge slot is configured to receive the connection bridge (26). The case housing (616) further includes a charging port (642), a wire (636), a case battery (644), a latch (638), and a motherboard (640). The charging port (642), such as a universal serial bus, is configured to receive an external cable (not shown) or connector (not shown) to communicate electrical power to the charging case (612) to charge the case battery (644) and/or the device battery (92). The charging port (642) is slidably coupled within the case housing (616) as shown in the present example.

In use, the charging case (612) may charge the case battery (644) or the device battery (92) via the external cable (not shown). In another example resonant charging (not shown), or inductive charging (not shown) may be used. The additional features described below to facilitate inductive or resonant charging would be incorporated into the charging case. For example, the charging case (612) would further include a coil (not shown). Additionally or in the alternative, the charging case (612) allows a patient to charge the device battery (92) remotely without receiving energy from the external cable (not shown). The charging case (612) may charge the device battery (92) with the case battery (644). For charging with an external cable (not shown), the external cable (not shown) is inserted into the charging port (642). A patient exhibits force longitudinally on the external cable (not shown), which in turn exhibits force longitudinally onto the charging port (642). In response to this force, the charging port (642) slides distally within the case housing (616) until a distal face of the charging port (642) engages a proximal face of the motherboard (640). Once the distal face of charging port (642) engages the proximal face of the motherboard (640), the latch (638), such as a spring or a hasp, grasps the charging port (642). The latch (638) holds the charging port (642) against the motherboard (640) maintaining electrical communication between the charging port (642) and the motherboard (640). Additionally, the latch (638) may include a detent feature (not shown) and/or a hinge (not shown). The motherboard (640) and the charging port (642) may have additional complementary electrical connectors (not shown) to facilitate the connection of the charging port (642) to the motherboard (640).

The motherboard (640) includes a CPU configured to regulate and control the charging of the batteries (644, 92). The motherboard (640) of the present example is positioned proximate to the charging port (642), however the motherboard (640) may be positioned anywhere within the charging case (612) with complementary electrical connectors (not shown). For example, the motherboard (640) may be positioned proximate to the charging plates (634). Additionally, the mother board (640) may act as a variable speed controller to reduce and increase the speed of the pumps based on an activity level, a metabolic condition, or an environmental condition. This variable speed controller may be used to conserve battery life.

The motherboard (640) as shown includes a left motherboard (640a) and a right motherboard (640b) but may be the single motherboard (640). The motherboard (640) is in further electrical communication with distal and proximal charging nodes (632, 634) via wires (636). The distal and proximal charging node (632, 634) are in electrical communication with the case battery (644) and are configured to distribute electrical energy to charge the case battery (644). Additionally, the charging nodes (632, 634) are in electrical communication with the device battery (92) via the distal and proximal annular charging plates (94, 96) and are configured to distribute electrical energy to charge the device battery (92). In the present example, the case battery (644) is located within the case housing (616). Alternatively or in addition, such case battery (644) may be further incorporated into the lid (618) for additional electrical energy storage capacity. In still other examples, alternative batteries may be removable and/or traditional storage batteries, such as a button cell, lithium ion battery.

IV. INDUCTIVE CHARGING FOR GAS CONCENTRATION DEVICE

Figure 16:
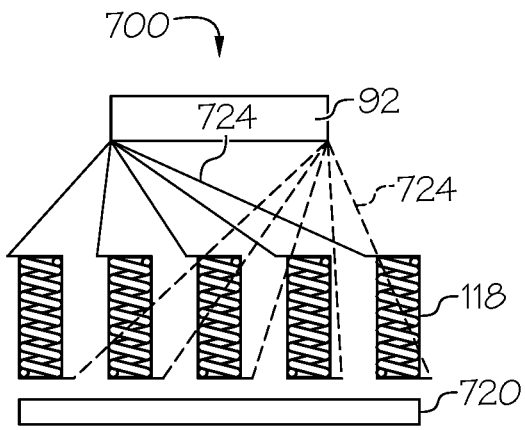
FIG. 16 depicts a schematic side elevational view of the charging case of FIG. 13A charging the gas concentration device of FIG. 1 via wireless inductive charging.

FIG. 16 shows a charging system (700) for the gas concentration device (10) (see FIG. 1). The charging system (700) includes the device battery (92) and the coil (118) discussed above in greater detail and a transmitter (720) configured to generate an inductive field. In this respect, the charging system (700) utilizes wireless inductive charging to charge device battery (92). In the present example, the transmitter (720) is brought into close proximity with the coil (118). Coil (118) acts as a receiver coil. The transmitter (720) uses an electromagnetic field to transfer energy to the coil (118) to charge the device battery (92) via wires (724). In one example, the charging system (700) incorporates the same coil (118) discussed above for pumping fluid as that used for charging the device battery (92), but it will be appreciated that alternative batteries and/or coils may be similarly used.

V. RESONANT CHARGING FOR GAS CONCENTRATION DEVICE

Figure 17:
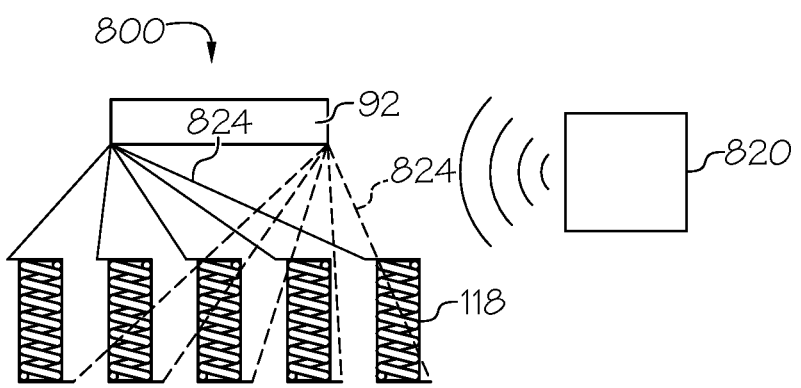
FIG. 17 depicts a schematic side elevational view of the charging case of FIG. 13A charging the gas concentration device of FIG. 1 via wireless frequency charging.

FIG. 17 shows another exemplary charging system (800) for the gas concentration device (10) (see FIG. 1). The charging system (800) is similar to the charging system (700) in some respects but differs from the charging system (700) in that the charging system (800) includes a resonant transformer (820) instead of the transmitter (720). This resonant transformer (820) transfers energy to the coil (118) via resonant frequencies that transfer power between coils (118) operating at identical resonant frequencies. The frequencies generated by the resonant transformer (820) create fields that interact with the coil (118). The resonant energy is transferred to the coil (118) generating a current and this transfers the energy to the device battery (92) via wires (824). Resonant power transfer allows wireless charging of device battery (92) from a greater distance than the inductive charging of FIG. 16. Resonant charging also allows for the magnetic field to be picked up from different areas in the coils (118) contrary to inductive charging where charging requires precise overlap of the transmitter coil (720) and the coils (118) to charge. Again, in one example, the charging system (800) incorporates the same coil (118) discussed above for pumping fluid as that used for charging the device battery (92), but it will be appreciated that alternative batteries and/or coils may be similarly used. Additional resonant circuits (not shown) to facilitate resonant charging may also be included.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A device for generating an enriched gas within a nasal vestibule of a patient, comprising: a housing having a distal housing portion and a proximal housing portion; a first chamber positioned within the housing and configured to be received within the nasal vestibule of the patient; at least a first chamber inlet fluidly connected to the first chamber; at least a first pump fluidly connected to the at least the first chamber inlet and configured to direct an ambient air from an ambient environment into the first chamber via the at least the first chamber inlet; a first molecular sieve bed positioned within the first chamber and configured to collect a predetermined molecule from the ambient air thereby generating the enriched gas; a first release outlet fluidly connected to the first chamber and configured to discharge the enriched gas from the first chamber into the nasal vestibule; and a first breath duct longitudinally extending through the housing and having a first distal duct opening and a first proximal duct opening, the first distal duct opening being positioned in the distal housing portion and the first proximal duct opening being positioned in the proximal housing portion such that the first breath duct is configured to fluidly communicate a first fluid flow through the housing for nasal breathing through the housing by the patient while the first chamber is positioned within the nasal vestibule of the patient.

Example 2

The device of Example 1, further comprising: a second chamber positioned within the housing and configured to be received within the nasal vestibule of the patient; at least a second chamber inlet fluidly connected to the second chamber; at least a second pump fluidly connected to the at least the second chamber inlet and configured to direct the ambient air from the ambient environment into the second chamber via the at least the second chamber inlet; a second molecular sieve bed positioned within the second chamber and configured to collect the predetermined molecule from the ambient air thereby generating the enriched gas; and a second release outlet fluidly connected to the second chamber and configured to discharge the enriched gas from the second chamber into the nasal vestibule.

Example 3

The device of any one or more of Examples 1 or 2, wherein the housing further includes a first lateral body, second lateral body, and a gap defined between the first and second lateral bodies configured to receive a nasal cartridge therebetween, wherein the first lateral body of the housing contains the first and second chambers.

Example 4

The device of any one or more of Examples 1 through 3, wherein the first breath duct is positioned laterally between the first and second chambers.

Example 5

The device of any one or more of Examples 1 through 4, further comprising a second breath duct extending through the housing and having a second distal duct opening and a second proximal duct opening, the second distal duct opening positioned in the distal housing portion and the second proximal duct opening in the proximal housing portion such that the second breath duct is configured to fluidly communicate a second fluid flow through the housing for nasal breathing through the housing by the patient while the second chamber is positioned within the nasal vestibule of the patient.

Example 6

The device of Example 5, wherein the housing further includes a first lateral body, a second lateral body, and a gap defined between the first and second lateral bodies configured to receive a nasal cartilage therebetween, wherein the first lateral body of the housing contains the first chamber and has the first breath duct extending therethrough, and wherein the second lateral body of the housing contains the second chamber and has the second breath duct extending therethrough.

Example 7

The device of any one or more of Examples 3 through 6, wherein the housing further includes a bridge laterally extending from the first lateral body to the second lateral body such that the bridge secures the first lateral body relative to the second lateral body.

Example 8

The device of Example 7, wherein the first lateral body has a first proximal body end portion and the second lateral body has a second proximal body end portion, and wherein the bridge is attached to each of the first and second proximal body end portions.

Example 9

The device of any one or more of Examples 1 through 8, wherein the first release outlet is fluidly connected to the first breath duct and thereby configured to discharge the enriched gas from the first chamber into the first breath duct.

Example 10

The device of any one or more of Examples 1 through 9, wherein the at least the first chamber inlet and the at least the first pump are positioned in the proximal housing portion.

Example 11

The device of any one or more of Examples 1 through 10, wherein the at least the first pump is positioned in the proximal housing portion such that the at least the first pump is proximally positioned relative to the first chamber.

Example 12

The device of any one or more of Examples 3 through 11, wherein the housing further includes a first lateral body extending along a first longitudinal axis and containing the first chamber, wherein the first lateral body defines a first outer profile about the first longitudinal axis and the at least the first pump is positioned within the first outer profile.

Example 13

The device of Example 12, wherein the at least the first pump includes a first plurality of first pumps configured to direct the ambient air from the ambient environment into the first chamber via the at least the first chamber inlet, and wherein each of the first plurality of first pumps is positioned within the first outer profile.

Example 14

The device of any one or more of Examples 12 or 13, further comprising: a second chamber contained within the first lateral body and configured to be received within the nasal vestibule of the patient; at least a second chamber inlet fluidly connected to the second chamber; a second plurality of second pumps fluidly connected to the at least the second chamber inlet and configured to direct the ambient air from the ambient environment into the second chamber via the at least the second chamber inlet; a second molecular sieve bed positioned within the second chamber and configured to collect the predetermined molecule from the ambient air thereby generating the enriched gas; and a second release outlet fluidly connected to the second chamber and configured to discharge the enriched gas from the second chamber into the nasal vestibule, wherein each of the second plurality of second pumps is positioned within the first outer profile of the first lateral body.

Example 15

The device of any one or more of Examples 3 through 14, further comprising: the housing further including a second lateral body extending along a second longitudinal axis and laterally offset from the first lateral body; a third chamber contained within the second lateral body and configured to be received within the nasal vestibule of the patient; at least a third chamber inlet fluidly connected to the third chamber; a third plurality of third pumps fluidly connected to the at least the third chamber inlet and configured to direct the ambient air from the ambient environment into the third chamber via the at least the third chamber inlet; a third molecular sieve bed positioned within the third chamber and configured to collect the predetermined molecule from the ambient air thereby generating the enriched gas; and a third release outlet fluidly connected to the third chamber and configured to discharge the enriched gas from the third chamber into the nasal vestibule, wherein the second lateral body defines a second outer profile about the second longitudinal axis and each of the third plurality of third pumps is positioned with the second outer profile.

Example 16

A device for generating an enriched gas within a nasal vestibule of a patient, comprising: a housing having a distal housing portion and a proximal housing portion; a first chamber positioned within the housing and configured to be received within the nasal vestibule of the patient; at least a first chamber inlet fluidly connected to the first chamber; a plurality of first pumps fluidly connected to the at least the first chamber inlet and configured to direct an ambient air from an ambient environment into the first chamber via the at least the first chamber inlet; a first molecular sieve bed positioned within the first chamber and configured to collect a predetermined molecule from the ambient air thereby generating the enriched gas; and a first release outlet fluidly connected to the first chamber and configured to discharge the enriched gas from the first chamber into the nasal vestibule, wherein each of the plurality of first pumps is positioned in the proximal housing portion such that the at least the first pump is proximally positioned relative to the first chamber.

Example 17

The device of Example 16, wherein the housing further includes a first lateral body extending along a first longitudinal axis and containing the first chamber, wherein the first lateral body defines a first outer profile about the first longitudinal axis and each of the plurality of first pumps is positioned within the first outer profile.

Example 18

The device of Example 17, further comprising: the housing further including a second lateral body extending along a second longitudinal axis and laterally offset from the first lateral body; a second chamber contained within the second lateral body and configured to be received within the nasal vestibule of the patient; at least a second chamber inlet fluidly connected to the second chamber; a second plurality of second pumps fluidly connected to the at least the second chamber inlet and configured to direct the ambient air from the ambient environment into the second chamber via the at least the second chamber inlet; a second molecular sieve bed positioned within the second chamber and configured to collect the predetermined molecule from the ambient air thereby generating the enriched gas; and a second release outlet fluidly connected to the second chamber and configured to discharge the enriched gas from the second chamber into the nasal vestibule, wherein the second lateral body defines a second outer profile about the second longitudinal axis and each of the second plurality of second pumps is positioned with the second outer profile.

Example 19

The device of Example 18, wherein the housing further includes a bridge laterally extending from the first lateral body to the second lateral body such that the bridge secures the first lateral body relative to the second lateral body.

Example 20

A method of generating an oxygen enriched gas for a patient, comprising collecting nitrogen from an ambient air into a molecular sieve bed positioned within a nasal vestibule of the patient thereby generating the oxygen enriched gas within the nasal vestibule of the patient.

Example 21

A device for moving ambient air into a gas generator comprising: a pump inlet proximally located, a pump outlet distally located, a piston chamber extending distally from the pump inlet, a piston located within the piston chamber, a duct conduit adjacent to the piston chamber and configured to be in fluid communication with the piston chamber, a chamber valve located proximate to the pump inlet, and a duct valve located proximate to the pump outlet.

Example 22

The device of Example 21, wherein the piston is sized to fit within the piston chamber with tolerances that allow some leakage around the piston to prevent hydrostatic lock.

Example 23

The device of any one or more of Examples 21 or 22, wherein the chamber valve is configured to allow leakage towards the pump inlet to prevent hydrostatic lock.

Example 23

The device of any one or more of Examples 21 through 23, further comprising a vent valve.

Example 24

A charging case for a gas generator comprising: a housing, a lid, a hinge, a charging port, and a battery.

Example 25

The device of Example 24, wherein the housing has a first bore configured to receive a first lateral body, and a second bore configured to accept a second lateral body.

Example 26

The device of any one or more of Examples 24 or 25, further comprising a charging node configured to align and communicate with a charging plate.

Example 27

The device of Example 26, further comprising a latch and a motherboard, wherein the latch is configured to retain and engage a charging cord within the charging port, and wherein the motherboard is in electrical communication with the charging cord when the latch retains and engages the charging cord.

Example 28

The device of Example 27, wherein the motherboard is configured to regulate the charging of the battery.

Example 28

A system comprising a charging case and a gas concentration device.

VII. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or immediately prior to use. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A device for generating an enriched gas within a nasal vestibule of a patient, comprising:
    a housing having a distal housing portion and a proximal housing portion;
    a first chamber positioned within the housing and configured to be received within the nasal vestibule of the patient;
    at least a first chamber inlet fluidly connected to the first chamber;
    at least a first pump fluidly connected to the at least the first chamber inlet and configured to direct an ambient air from an ambient environment into the first chamber via the at least the first chamber inlet;
    a first molecular sieve bed positioned within the first chamber and configured to collect a predetermined molecule from the ambient air thereby generating the enriched gas;
    a first release outlet fluidly connected to the first chamber and configured to discharge the enriched gas from the first chamber into the nasal vestibule;
    a first breath duct longitudinally extending through the housing and having a first distal duct opening and a first proximal duct opening, the first distal duct opening being positioned in the distal housing portion and the first proximal duct opening being positioned in the proximal housing portion such that the first breath duct is configured to fluidly communicate a first fluid flow through the housing for nasal breathing through the housing by the patient while the first chamber is positioned within the nasal vestibule of the patient;
    a second chamber positioned within the housing and configured to be received within the nasal vestibule of the patient; and
    a second breath duct extending through the housing and having a second distal duct opening and a second proximal duct opening, the second distal duct opening positioned in the distal housing portion and the second proximal duct opening in the proximal housing portion such that the second breath duct is configured to fluidly communicate a second fluid flow through the housing for nasal breathing through the housing by the patient while the second chamber is positioned within the nasal vestibule of the patient, and
    wherein the housing further includes a first lateral body, a second lateral body, and a gap defined between the first and second lateral bodies configured to receive a nasal cartilage therebetween, wherein the first lateral body of the housing contains the first chamber and has the first breath duct extending therethrough, and wherein the second lateral body of the housing contains the second chamber and has the second breath duct extending therethrough.

2. The device of claim 1, further comprising:
    at least a second chamber inlet fluidly connected to the second chamber;
    at least a second pump fluidly connected to the at least the second chamber inlet and configured to direct the ambient air from the ambient environment into the second chamber via the at least the second chamber inlet;
    a second molecular sieve bed positioned within the second chamber and configured to collect the predetermined molecule from the ambient air thereby generating the enriched gas; and
    a second release outlet fluidly connected to the second chamber and configured to discharge the enriched gas from the second chamber into the nasal vestibule.

3. The device of claim 2, further comprising a third chamber positioned within the housing, wherein the first lateral body of the housing contains the first and third chambers.

4. The device of claim 3, wherein the first breath duct is positioned laterally between the first and third chambers.

5. The device of claim 1, wherein the housing further includes a bridge laterally extending from the first lateral body to the second lateral body such that the bridge secures the first lateral body relative to the second lateral body.

6. The device of claim 5, wherein the first lateral body has a first proximal body end portion and the second lateral body has a second proximal body end portion, and wherein the bridge is attached to each of the first and second proximal body end portions.

7. The device of claim 1, wherein the first release outlet is fluidly connected to the first breath duct and thereby configured to discharge the enriched gas from the first chamber into the first breath duct.

8. The device of claim 7, wherein the at least the first chamber inlet and the at least the first pump are positioned in the proximal housing portion.

9. The device of claim 1, wherein the at least the first pump is positioned in the proximal housing portion such that the at least the first pump is proximally positioned relative to the first chamber.

10. The device of claim 9, wherein the housing further includes the first lateral body extending along a first longitudinal axis and containing the first chamber, wherein the first lateral body defines a first outer profile about the first longitudinal axis and the at least the first pump is positioned within the first outer profile.

11. The device of claim 10, wherein the at least the first pump includes a first plurality of first pumps configured to direct the ambient air from the ambient environment into the first chamber via the at least the first chamber inlet, and wherein each of the first plurality of first pumps is positioned within the first outer profile.

12. The device of claim 11, further comprising:
    a third chamber contained within the first lateral body and configured to be received within the nasal vestibule of the patient;
    at least a third chamber inlet fluidly connected to the third chamber;
    a third plurality of third pumps fluidly connected to the at least the third chamber inlet and configured to direct the ambient air from the ambient environment into the third chamber via the at least the third chamber inlet;
    a third molecular sieve bed positioned within the third chamber and configured to collect the predetermined molecule from the ambient air thereby generating the enriched gas; and a third release outlet fluidly connected to the third chamber and configured to discharge the enriched gas from the third chamber into the nasal vestibule,
wherein each of the third plurality of third pumps is positioned within the first outer profile of the first lateral body.

13. The device of claim 12, further comprising:
the housing further including the second lateral body extending along a second longitudinal axis and laterally offset from the first lateral body;
a fourth chamber contained within the second lateral body and configured to be received within the nasal vestibule of the patient;
at least a fourth chamber inlet fluidly connected to the fourth chamber;
a fourth plurality of fourth pumps fluidly connected to the at least the fourth chamber inlet and configured to direct the ambient air from the ambient environment into the fourth chamber via the at least the fourth chamber inlet;
a fourth molecular sieve bed positioned within the fourth chamber and configured to collect the predetermined molecule from the ambient air thereby generating the enriched gas; and
a fourth release outlet fluidly connected to the fourth chamber and configured to discharge the enriched gas from the fourth chamber into the nasal vestibule,
wherein the second lateral body defines a second outer profile about the second longitudinal axis and each of the fourth plurality of fourth pumps is positioned with the second outer profile.

14. A device for generating an enriched gas within a nasal vestibule of a patient, comprising:
a housing having a distal housing portion and a proximal housing portion;
a first chamber positioned within the housing and configured to be received within the nasal vestibule of the patient;
at least a first chamber inlet fluidly connected to the first chamber;
a plurality of first pumps fluidly connected to the at least the first chamber inlet and configured to direct an ambient air from an ambient environment into the first chamber via the at least the first chamber inlet;
a first molecular sieve bed positioned within the first chamber and configured to collect a predetermined molecule from the ambient air thereby generating the enriched gas; and
a first release outlet fluidly connected to the first chamber and configured to discharge the enriched gas from the first chamber into the nasal vestibule,
wherein each of the plurality of first pumps is positioned in the proximal housing portion such that the at least the first pump is proximally positioned relative to the first chamber,
wherein the housing further includes a first lateral body extending along a first longitudinal axis and containing the first chamber, wherein the first lateral body defines a first outer profile about the first longitudinal axis and each of the plurality of first pumps is positioned within the first outer profile.

15. The device of claim 14, further comprising:
the housing further including a second lateral body extending along a second longitudinal axis and laterally offset from the first lateral body;
a second chamber contained within the second lateral body and configured to be received within the nasal vestibule of the patient;
at least a second chamber inlet fluidly connected to the second chamber;
a second plurality of second pumps fluidly connected to the at least the second chamber inlet and configured to direct the ambient air from the ambient environment into the second chamber via the at least the second chamber inlet;
a second molecular sieve bed positioned within the second chamber and configured to collect the predetermined molecule from the ambient air thereby generating the enriched gas; and
a second release outlet fluidly connected to the second chamber and configured to discharge the enriched gas from the second chamber into the nasal vestibule,
wherein the second lateral body defines a second outer profile about the second longitudinal axis and each of the second plurality of second pumps is positioned with the second outer profile.

16. The device of claim 15, wherein the housing further includes a bridge laterally extending from the first lateral body to the second lateral body such that the bridge secures the first lateral body relative to the second lateral body.

17. A device for generating an enriched gas within a nasal vestibule of a patient, comprising:
a housing having a distal housing portion and a proximal housing portion;
a first chamber and a second chamber positioned within the housing and configured to be received within the nasal vestibule of the patient;
at least a first chamber inlet fluidly connected to the first chamber;
at least a first pump fluidly connected to the at least the first chamber inlet and configured to direct an ambient air from an ambient environment into the first chamber via the at least the first chamber inlet;
a first molecular sieve bed positioned within the first chamber and configured to collect a predetermined molecule from the ambient air thereby generating the enriched gas;
a first release outlet fluidly connected to the first chamber and configured to discharge the enriched gas from the first chamber into the nasal vestibule; and
a first breath duct longitudinally extending through the housing and having a first distal duct opening and a first proximal duct opening, the first distal duct opening being positioned in the distal housing portion and the first proximal duct opening being positioned in the proximal housing portion such that the first breath duct is configured to fluidly communicate a first fluid flow through the housing for nasal breathing through the housing by the patient while the first chamber is positioned within the nasal vestibule of the patient,
wherein the housing further includes a first lateral body, a second lateral body, and a gap defined between the first and second lateral bodies configured to receive a nasal cartilage therebetween, wherein the first lateral body of the housing contains the first and second chambers.

18. The device of claim 17, further comprising:
at least a second chamber inlet fluidly connected to the second chamber;
at least a second pump fluidly connected to the at least the second chamber inlet and configured to direct the ambient air from the ambient environment into the second chamber via the at least the second chamber inlet;

a second molecular sieve bed positioned within the second chamber and configured to collect the predetermined molecule from the ambient air thereby generating the enriched gas; and a second release outlet fluidly connected to the second chamber and configured to discharge the enriched gas from the second chamber into the nasal vestibule.

19. The device of claim 18, wherein the first breath duct is positioned laterally between the first and second chambers.

* * * * *